(12) United States Patent
Domon et al.

(10) Patent No.: US 9,500,949 B2
(45) Date of Patent: Nov. 22, 2016

(54) CHEMICALLY-AMPLIFIED POSITIVE RESIST COMPOSITION AND RESIST PATTERNING PROCESS USING THE SAME

(71) Applicant: SHIN-ETSU CHEMICAL CO., LTD., Tokyo (JP)

(72) Inventors: Daisuke Domon, Jyoetsu (JP); Keiichi Masunaga, Jyoetsu (JP); Satoshi Watanabe, Jyoetsu (JP); Masaki Ohashi, Jyoetsu (JP); Masahiro Fukushima, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/625,892

(22) Filed: Feb. 19, 2015

(65) Prior Publication Data
US 2015/0253664 A1 Sep. 10, 2015

(30) Foreign Application Priority Data
Mar. 7, 2014 (JP) ................................. 2014-044510

(51) Int. Cl.
| | | |
|---|---|---|
| G03F 7/004 | (2006.01) |
| C07C 61/135 | (2006.01) |
| C07C 61/15 | (2006.01) |
| C07C 61/26 | (2006.01) |
| C07C 61/28 | (2006.01) |
| C07C 61/39 | (2006.01) |
| C07C 61/40 | (2006.01) |
| C07C 63/08 | (2006.01) |
| C07C 63/68 | (2006.01) |
| C07C 69/76 | (2006.01) |
| G03F 7/039 | (2006.01) |
| G03F 7/20 | (2006.01) |

(52) U.S. Cl.
CPC ........... *G03F 7/0045* (2013.01); *C07C 61/135* (2013.01); *C07C 61/15* (2013.01); *C07C 61/26* (2013.01); *C07C 61/28* (2013.01); *C07C 61/39* (2013.01); *C07C 61/40* (2013.01); *C07C 63/08* (2013.01); *C07C 63/68* (2013.01); *C07C 69/76* (2013.01); *G03F 7/0046* (2013.01); *G03F 7/0392* (2013.01); *G03F 7/0395* (2013.01); *G03F 7/0397* (2013.01); *G03F 7/2041* (2013.01)

(58) Field of Classification Search
CPC .. G03F 7/0045; G03F 7/0392; G03F 7/0397; C07C 61/135; C07C 61/15; C07C 61/26; C07C 61/28; C07C 61/39; C07C 61/40; C07C 63/08; C07C 63/68; C07C 69/76
USPC ..................... 430/270.1, 905, 910, 921, 922; 562/409, 499, 501, 502, 510
See application file for complete search history.

(56) References Cited

U.S. PATENT DOCUMENTS

| | | | |
|---|---|---|---|
| 9,256,127 B2 * | 2/2016 | Sagehashi | G03F 7/0397 |
| 2001/0036589 A1 | 11/2001 | Kinoshita et al. | |
| 2007/0281242 A1 | 12/2007 | Hu et al. | |
| 2008/0118860 A1 | 5/2008 | Harada et al. | |
| 2009/0226672 A1 * | 9/2009 | Meador | G03F 7/039 428/161 |
| 2010/0136477 A1 * | 6/2010 | Ng | G03F 7/0045 430/270.1 |
| 2010/0316955 A1 | 12/2010 | Masunaga et al. | |
| 2011/0014567 A1 * | 1/2011 | Ichikawa | C07C 62/22 430/270.1 |
| 2011/0171577 A1 | 7/2011 | Tsuchimura et al. | |
| 2011/0212391 A1 | 9/2011 | Masunaga et al. | |
| 2012/0083580 A1 | 4/2012 | Kinsho et al. | |

(Continued)

FOREIGN PATENT DOCUMENTS

| | | |
|---|---|---|
| CN | 1832982 A | 9/2006 |
| CN | 102321212 A | 1/2012 |

(Continued)

OTHER PUBLICATIONS

Aug. 20, 2015 Office Action issued in Taiwanese Patent Application No. 104106950.

*Primary Examiner* — John S Chu
(74) *Attorney, Agent, or Firm* — Oliff PLC

(57) ABSTRACT

The present invention provides a chemically-amplified positive resist composition including a sulfonium salt capable of providing a pattern having an extremely high resolution with low line edge roughness, and also provides a resist patterning process using the same.

The present invention was accomplished by a chemically-amplified positive resist composition including: (A) a salt represented by the following general formula (1); and (B) a resin containing a repeating unit represented by the following general formula (U-1) that dissolves by acid action and increases solubility in an alkaline developer, and a resist patterning process using the same.

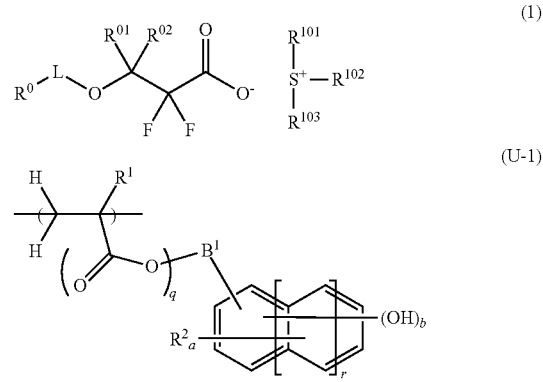

20 Claims, No Drawings

(56) References Cited

U.S. PATENT DOCUMENTS

| | | |
|---|---|---|
| 2013/0034813 A1 | 2/2013 | Ohsawa et al. |
| 2013/0084438 A1* | 4/2013 | Iwato ............... G03F 7/0392 428/195.1 |
| 2013/0183621 A1* | 7/2013 | Ohashi ............... G03F 7/004 430/270.1 |
| 2015/0268556 A1* | 9/2015 | Domon ............... G03F 7/30 430/5 |
| 2015/0323865 A1* | 11/2015 | Sagehashi ............ G03F 7/0397 430/285.1 |

FOREIGN PATENT DOCUMENTS

| | | |
|---|---|---|
| JP | H11-327143 A | 11/1999 |
| JP | 2004-115630 A | 4/2004 |
| JP | 3955384 B2 | 8/2007 |
| JP | 2008-111103 A | 5/2008 |
| JP | 2009-053518 A | 3/2009 |
| JP | 4231622 B2 | 3/2009 |
| JP | 2010-100604 A | 5/2010 |
| JP | 2011-022564 A | 2/2011 |
| JP | 2012-097256 A | 5/2012 |
| JP | 5083528 B2 | 11/2012 |

* cited by examiner

CHEMICALLY-AMPLIFIED POSITIVE RESIST COMPOSITION AND RESIST PATTERNING PROCESS USING THE SAME

BACKGROUND OF THE INVENTION

1. Field of the Invention

The present invention relates to a chemically-amplified positive resist composition used for processing a semiconductor and a photo mask blank, and a resist patterning process using the same.

2. Description of the Related Art

In recent years, as an integrated circuit progresses toward a high integration, a further finer patterning is required. When a resist pattern of 0.2 µm or less is processed, as a usual manner, a chemically amplified resist composition in which an acid acts as a catalyst has been used. As the exposure light source, a high energy beam such as an ultraviolet beam, a far-ultraviolet beam and an electron beam has been used, and especially, electron beam lithography, which is used as ultrafine processing technique, has become indispensable as a method of processing a photo mask blank in producing a photomask used for semiconductor manufacturing.

Polymers having a large amount of aromatic skeleton with acidic side chain, such as polyhydroxystyrene, have been favorably used as a resist composition for KrF excimer laser, but not for ArF excimer laser because they exhibit large absorption to light whose wavelength is approximately 200 nm. Due to high etching resistance, however, this type of polymer essentially serves as a useful resist composition for electron beam to form a finer pattern than a processing limit using an ArF excimer laser and as a resist composition for extreme ultraviolet (EUV).

Normally, a base polymer of a positive resist composition for electron beam or a resist composition for EUV is mainly composed of a material that solubilizes in an alkaline developer. Specifically, the solubilization is performed by subjecting an acid-soluble protective group masking an acid functional group of a phenol side chain in a base polymer to deprotection with use of an acid generated from a photo acid generator by high energy beam exposure as a catalyst. In addition, the acid-soluble protective group mainly includes a tertiary alkyl group, a t-butoxycarbonyl group and an acetal group. Herein, use of a protective group having a relatively low activation energy required for deprotection such as an acetal group can advantageously provide a resist film with high sensitivity. However, if acid diffusion generated is insufficiently controlled, a deprotection reaction is caused even in a non-exposed area in a resist film, leading to such technical problems as deterioration of a line edge roughness (LER) and decline in in-plane uniformity (CDU) of a pattern line width.

To control the resist sensitivity and pattern profile, various improvements have been achieved according to the way materials used in a resist composition are selected, combined and processed. One of its improvements is to control acid diffusion. Acid diffusion has been extensively discussed, because it can significantly affect sensitivity and resolution of a chemically-amplified resist.

Patent Documents 1 and 2 describe an example of controlling acid diffusion to reduce roughness by making bulky a benzenesulfonic acid generated from a photo acid generator by exposure. However, since the degree of the acid diffusion control remains insufficient, development of an acid generator with reduced diffusion has been desired.

In addition, Patent Document 3 describes an example of controlling acid diffusion by bonding a sulfonic acid generated by exposure to a resin used in a resist composition. The method for controlling acid diffusion by bonding a repeating unit that generates an acid by exposure to a base polymer is effective in obtaining a pattern with low LER. However, according to the structure and introduction ratio of the repeating unit, a base polymer obtained by bonding the repeating unit that generates an acid by exposure has a problematic solubility to an organic solvent.

In addition, use of a sulfonium salt that generates an acid having a high acid strength such as fluorinated alkanesulfonic acid and a resin comprising a repeating unit having an acetal group described in Patent Document 4 can form a pattern with a high LER. Specifically, since the acid strength of fluorinated alkanesulfonic acid is too high for deprotection of an acetal group having a relatively low activation energy therefor, even control of acid diffusion can make a progressive deprotection reaction by a slight amount of an acid that has diffused into a non-exposed area. This is also found in a sulfonium salt that generates a benzenesulfonic acid described in the Patent Documents 1 and 2. Therefore, development of an acid generator that generates more desirably strong acid for deprotection of an acetal group is being desired.

In order to control acid diffusion, improvement in acid diffusion control agent (called also as "quencher") is required, in addition to the method for making bulky the acid generated.

Acid diffusion control agent is substantially essential component to control acid diffusion and improve resist performance. Development of an acid diffusion control agent has conventionally been discussed in various manners, and amine and acidulous onium salt are commonly used. As for an example of the acidulous onium salt, Patent Document 5 describes that the addition of triphenyl sulfonium acetate enables a favorable resist pattern without T-top shape, line width difference between a dense pattern and an isolated pattern, and standing wave to be formed. Patent Document 6 describes improvement in sensitivity, resolution and exposure margin by addition of a sulfonic acid organic salt or a carboxylic acid organic salt. Patent Document 7 describes that a resist compositions for KrF and electron beam that contain a photo acid generator generating a fluorine-containing carboxylic acid is excellent in resolution, and improves process allowability such as exposure margin and focal depth. In these technologies, a strong acid generated from other photo acid generators by exposure (sulfonic acid) exchanges with an acidulous onium salt to produce weak acid and strong acid onium salt. Accordingly, by substituting a strong acid of high acidity (sulfonic acid) with a weak acid (carboxylic acid), acid decomposition reaction of an acid-labile group is controlled to achieve a smaller interval for acid diffusion. Apparently, the resulting product functions as an acid diffusion control agent.

However, use of the-described resist composition containing a carboxylic acid onium salt or a fluorocarboxylic acid onium salt for patterning can cause a higher LER. Thus, development of an acid diffusion control agent capable of reducing LER has been desired.

PRIOR ART DOCUMENTS

Patent Documents

Patent Document 1: Japanese Patent Laid-Open Publication No. 2009-053518

Patent Document 2: Japanese Patent Laid-Open Publication No. 2010-100604

Patent Document 3: Japanese Patent Laid-Open Publication No. 2011-22564

Patent Document 4: Japanese Patent No. 5083528 Patent Document 5: Japanese Patent No. 3955384

Patent Document 6: Japanese Patent Laid-Open Publication No. H11-327143

Patent Document 7: Japanese Patent No. 4231622

SUMMARY OF THE INVENTION

The present invention has been accomplished to solve the above-mentioned problems, and an object thereof is to provide a chemically-amplified positive resist composition capable of improving the resolution for patterning and obtaining a pattern with reduced line edge roughness (LER).

To solve the above-mentioned problems, the present invention provides a chemically-amplified positive resist composition for high energy beam exposure comprising: (A) a salt represented by the following general formula (1); and (B) a resin containing a repeating unit represented by the following general formula (U-1) that dissolves by acid action and increases solubility in an alkaline developer,

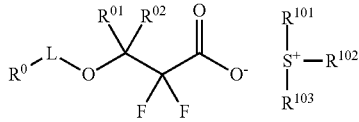

(1)

wherein $R^0$ represents a hydrogen atom, or a linear monovalent hydrocarbon group having 1 to 20 carbon atoms or a branched or a cyclic monovalent hydrocarbon group having 3 to 20 carbon atoms with which a hetero atom may be substituted or in which a hetero atom may be included; each $R^{01}$ and $R^{02}$ independently represents a hydrogen atom, or a linear monovalent hydrocarbon group having 1 to 20 carbon atoms or a branched or a cyclic monovalent hydrocarbon group having 3 to 20 carbon atoms with which a hetero atom may be substituted or in which a hetero atom may be included, and $R^{01}$ and $R^{02}$ may mutually be bonded to form a cyclic structure together with a carbon atom bonded by the same and a carbon atom between the same, and at least one of $R^0$, $R^{01}$ and $R^{02}$ has a cyclic structure; each $R^{101}$, $R^{102}$ and $R^{103}$ independently represents a linear monovalent hydrocarbon group having 1 to 20 carbon atoms or a branched or a cyclic monovalent hydrocarbon group having 3 to 20 carbon atoms with which a hetero atom may be substituted or in which a hetero atom may be included, and two or more of $R^{101}$, $R^{102}$ and $R^{103}$ may mutually be bonded to form a cyclic structure together with a sulfur atom in the formula; and L represents a single bond, or any of an ester bond, a sulfonic acid ester bond, a carbonate bond, and a carbamate bond, each of which is formed together with an adjacent oxygen atom,

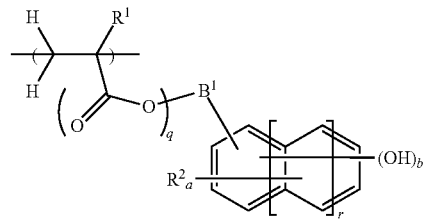

(U-1)

wherein "q" represents 0 or 1; "r" represents an integer of 0 to 2; $R^1$ represents any of a hydrogen atom, a fluorine atom, a methyl group, and a trifluoromethyl group; each $R^2$ independently represents a hydrogen atom or an alkyl group having 1 to 6 carbon atoms; $B^1$ represents a single bond, or an alkylene group having 1 to 10 carbon atoms that may contain an ether bond; "a" represents an integer satisfying a≤+2r−b; and "b" represents an integer of 1 to 3.

The resist composition can effectively control acid diffusion by exposure in patterning by action of the salt, and improve the resolution and obtain a pattern with a reduced LER when a pattern is formed by coating for a resist film. Also, by the action of the repeating unit, the solubility to an alkaline developer is favorable and when coating for a resist film, the adhesiveness to a substrate to be processed can be improved.

It is preferable that the resin further contain a repeating unit represented by the following general formula (U-2),

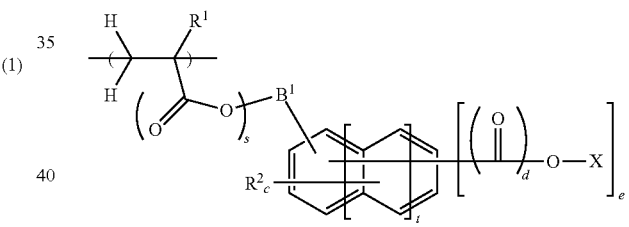

(U-2)

wherein "s" represents 0 or 1; "t" represents an integer of 0 to 2; $R^1$, $R^2$, and $B^1$ are the same as before; "c" represents an integer satisfying c≤+2 t−e; "d" represents 0 or 1; "e" represents an integer of 1 to 3; and X represents an acid labile group if "e" represents 1 and a hydrogen atom or an acid labile group if "e" represents 2 or more, but at least one thereof represents an acid labile group.

The resist composition shows more favorable solubility to an alkaline developer, because an acid-labile group, or a protective group in the repeating unit causes a deprotection reaction by acid action.

It is also preferable that the resin further contain at least one of repeating units represented by the following general formulae (U-3) and (U-4),

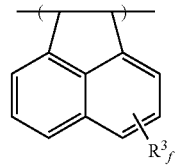

(U-3)

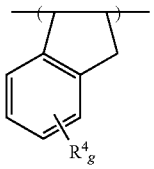

(U-4)

wherein "f" represents an integer of 0 to 6; each $R^3$ independently represents any of a hydrogen atom, an alkyl group or a primary or a secondary alkoxy group having 1 to 6 carbon atoms that may be halogen-substituted, and an alkylcarbonyloxy group having 1 to 7 carbon atoms that may be halogen-substituted; "g" represents an integer of 0 to 4; each $R^4$ independently represents any of a hydrogen atom, an alkyl or a primary or a secondary alkoxy group having 1 to 6 carbon atoms that may be halogen-substituted, and an alkylcarbonyloxy group having 1 to 7 carbon atoms that may be halogen-substituted.

The resist composition can improve etching resistance by action of the repeating unit.

Also, the resist composition preferably contains an acid generator that generates a sulfonic acid by high energy beam exposure.

The resist composition can preferably be used as a chemically-amplified positive resist composition.

In addition, the resist composition preferably further contains a basic compound.

The resist composition can control acid diffusion more effectively, achieve more favorable resolution, and obtain a pattern with reduced LER.

Further, the present invention provides a resist patterning process comprising steps of: applying the resist composition on a substrate to be processed to obtain a resist film; pattern-exposing by a high energy beam; and developing by using an alkaline developer.

In the resist patterning process, acid diffusion during exposure can be effectively controlled by action of the salt contained in the resist composition. Therefore, a pattern having excellent resolution with reduced LER can be formed on a resist film.

At this time, an EUV or an electron beam is preferably used as the high energy beam.

In such a manner, a finer pattern can be formed on a resist film.

At this time, a top surface of the substrate to be processed is preferably composed of a material containing chrome.

Also, a photo mask blank is preferably used as the substrate to be processed.

Accordingly, the resist patterning process of the present invention can obtain a resist film excellent in adhesiveness and form a pattern with reduced LER by exposure, even by using a substrate to be processed (e.g. a photo mask blank) whose top surface is composed of a material that readily affects a resist pattern shape such as a material containing chrome.

The chemically-amplified positive resist composition of the present invention can effectively control a diffusion of an acid generated by exposure, and obtain a pattern having an extremely high resolution for patterning with reduced LER. In addition, the inventive resist patterning process using the above chemically-amplified positive resist composition enables a pattern having high resolution with reduced LER to be formed, resulting in preferable availability in fine processing technique, particularly in EUV and EB lithography.

DETAILED DESCRIPTION OF THE PREFERRED EMBODIMENTS

Inventors of the present invention have carried out extended research and found that a sulfonium salt of a carboxylic acid with which a fluorine atom is substituted at α position is introduced into a resist composition to obtain a pattern with low LER. Based on that information, the present invention was accomplished.

The present invention will be described in detail. In the following description, some chemical structures represented by chemical formulae contain an asymmetric carbon, thus including an enantiomer and a diastereomer. In this case, these isomers are collectively represented by one common formula. These isomers may be used alone or as a mixture.

The present invention provides a chemically-amplified positive resist composition for high energy beam exposure comprising: (A) a salt represented by the following general formula (1); and (B) a resin that dissolves by acid action and increases solubility in an alkaline developer (hereinafter referred to as a base resin).

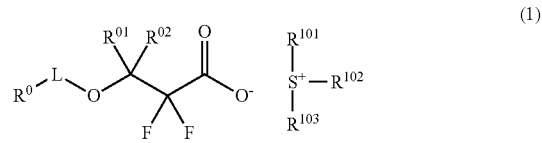

(1)

In the general formula (1), $R^0$ represents a hydrogen atom, or a linear monovalent hydrocarbon group having 1 to 20 carbon atoms or a branched or a cyclic monovalent hydrocarbon group having 3 to 20 carbon atoms with which a hetero atom may be substituted or in which a hetero atom may be included.

Illustrative example of $R^0$ includes a methyl group, an ethyl group, a propyl group, an isopropyl group, an n-butyl group, a sec-butyl group, a tert-butyl group, a tert-amyl group, an n-pentyl group, an n-hexyl group, an n-octyl group, an n-nonyl group, an n-decyl group, a cyclopentyl group, a cyclohexyl group, a 2-ethylhexyl group, a cyclopentylmethyl group, a cyclopentylethyl group, a cyclopentylbutyl group, a cyclohexylmethyl group, a cyclohexylethyl group, a cyclohexylbutyl group, a norbornyl group, a tricyclo[5.2.1.0$^{2,6}$]decanyl group, an adamantyl group, an adamantylmethyl group, a phenyl group, a naphthyl group, and an anthracenyl group. A part of hydrogen atoms of these groups may be substituted with a hetero atom such as oxygen atom, sulfur atom, nitrogen atom and halogen atom, and a hetero atom such as oxygen atom, sulfur atom and nitrogen atom may be included. Specifically, a hydroxy group, a cyano group, a carbonyl group, an ether bond, an ester bond, a sulfonic acid ester bond, a carbonate bond, a lactone ring, a sultone ring, a carboxylic anhydride, a haloalkyl group and so on may be formed or included.

In the general formula (1), each $R^{01}$ and $R^{02}$ independently represents a hydrogen atom, or a linear monovalent hydrocarbon group having 1 to 20 carbon atoms or a branched or a cyclic monovalent hydrocarbon group having 3 to 20 carbon atoms with which a hetero atom may be substituted or in which a hetero atom may be included. $R^{01}$ and $R^{02}$ may mutually be bonded to form a cyclic structure together with a carbon atom bonded by the same and a carbon atom between the same.

A monovalent hydrocarbon group can be illustrated as shown in illustrative example of $R^0$. When $R^{01}$ and $R^{02}$ are mutually bonded to form a cyclic structure together with a carbon atom bonded by the same and a carbon atom between the same, illustrative example of a formed cyclic substituent includes a cyclopentyl group, a cyclohexyl group, a norbornyl group, and an adamantyl group, and part of hydrogen atoms of these groups may be substituted with a hetero atom such as oxygen atom, sulfur atom, nitrogen atom, and halogen atom, and a hetero atom such as oxygen atom, sulfur atom, and nitrogen atom may be included. Specifically, a hydroxy group, a cyano group, a carbonyl group, an ether bond, an ester bond, a sulfonic acid ester bond, a carbonate bond, a lactone ring, a sultone ring, a carboxylic anhydride, a haloalkyl group and so on may be formed or included.

In addition, at least one of $R^0$, $R^{01}$ and $R^{02}$ has a cyclic structure. Illustrative example of a cyclic group includes a cyclopentyl group, a cyclohexyl group, a norbornyl group, a tricyclo[5.2.1.0$^{2,6}$]decanyl group, an adamantyl group, a phenyl group, a naphthyl group, and an anthracenyl group, and part of hydrogen atoms of these groups may be substituted with a hetero atom such as oxygen atom, sulfur atom, nitrogen atom, and halogen atom, and a hetero atom such as oxygen atom, sulfur atom, and nitrogen atom may be included. Specifically, a hydroxy group, a cyano group, a carbonyl group, an ether bond, an ester bond, a sulfonic acid ester bond, a carbonate bond, a lactone ring, a sultone ring, a carboxylic anhydride, a haloalkyl group and so on may be formed or included. Illustrative example of the preferable cyclic group includes an alicyclic hydrocarbon group.

L in the general formula (1) represents a single bond or any of an ester bond, a sulfonic acid ester bond, a carbonate bond and a carbamate bond each of which is formed together with an adjacent oxygen atom.

Illustrative example of a preferable structure at an anion portion of a sulfonium salt represented by the general formula (1) is shown as follows.

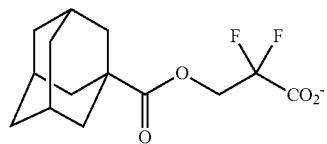
(A-1)

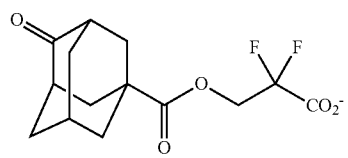
(A-2)

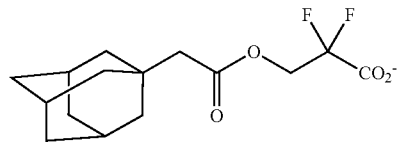
(A-3)

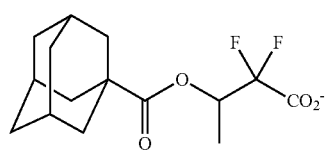
(A-4)

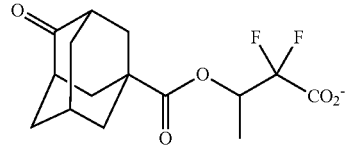
(A-5)

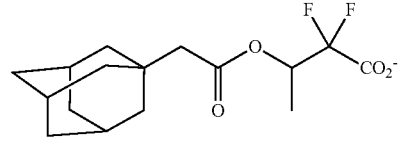
(A-6)

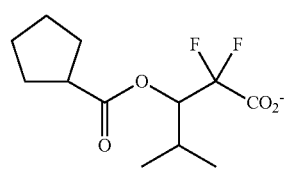
(A-7)

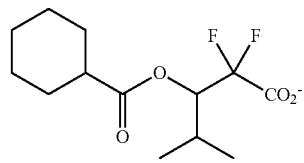
(A-8)

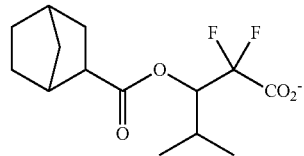
(A-9)

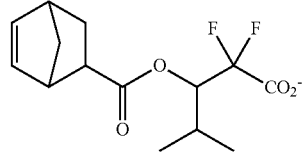
(A-10)

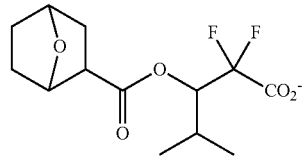
(A-11)

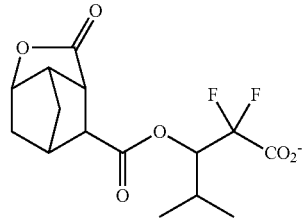
(A-12)

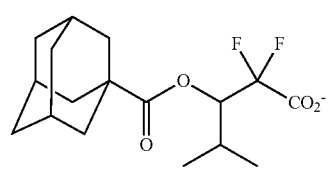
(A-13)

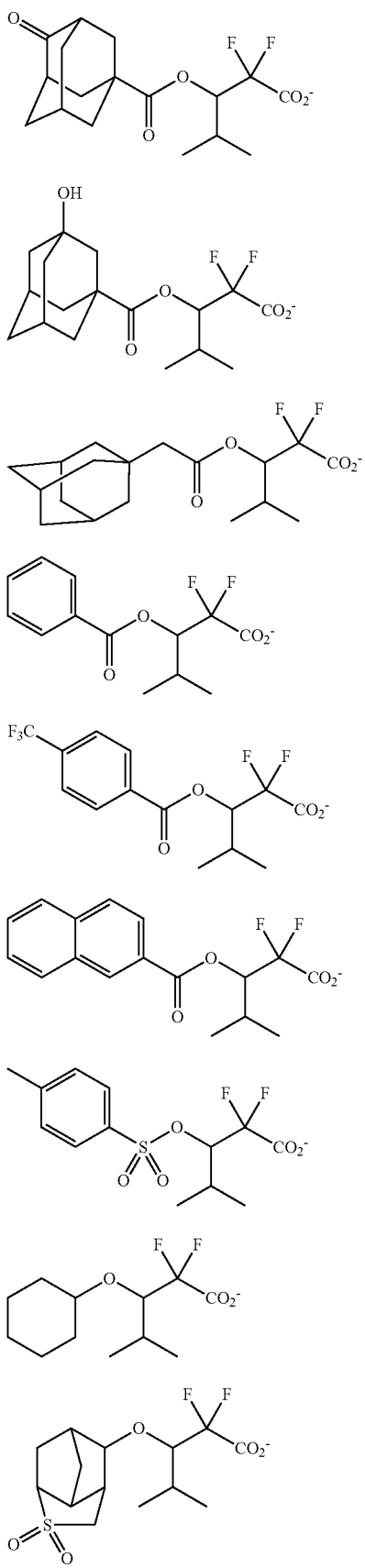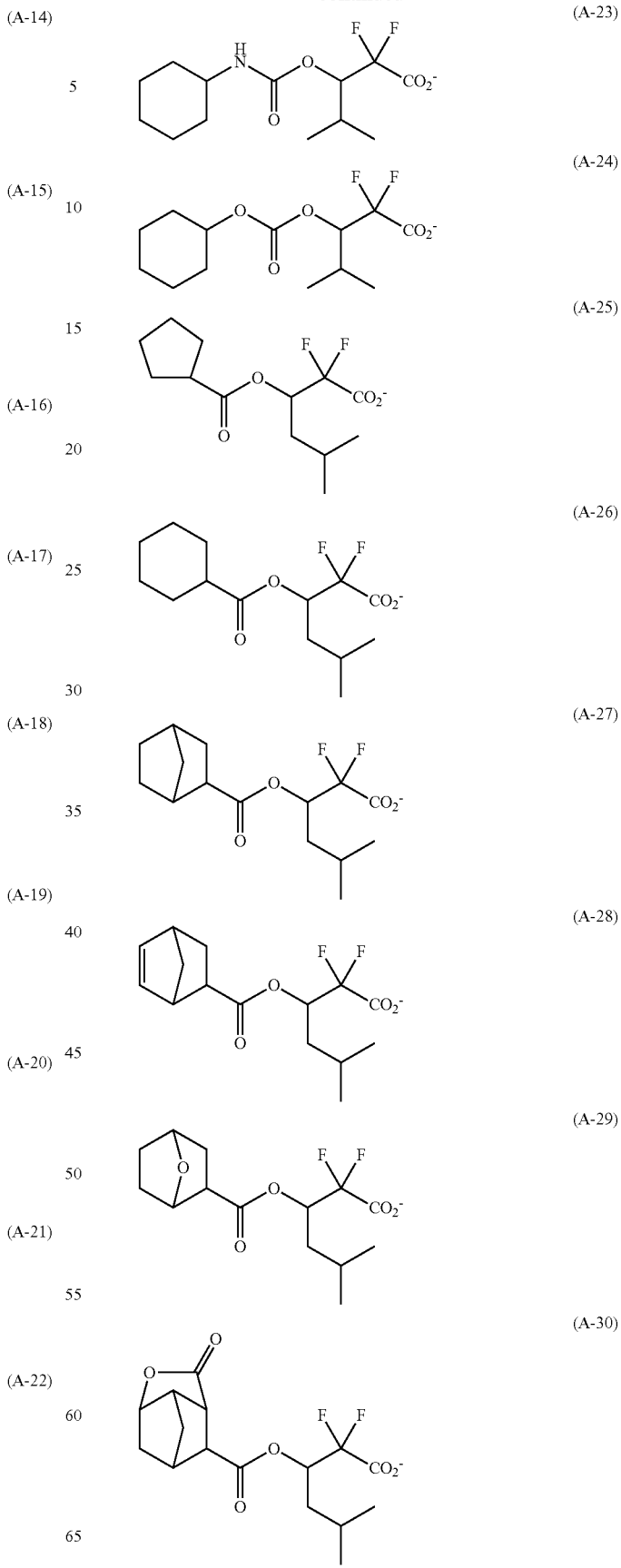

-continued
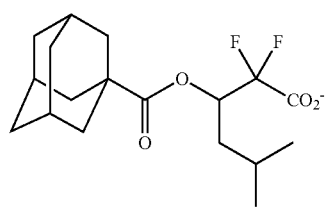 (A-31)
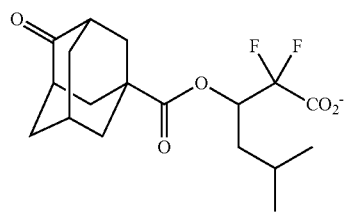 (A-32)
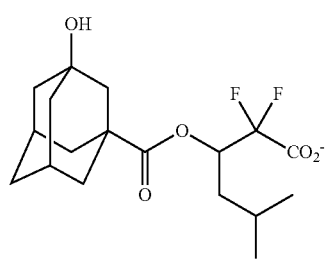 (A-33)
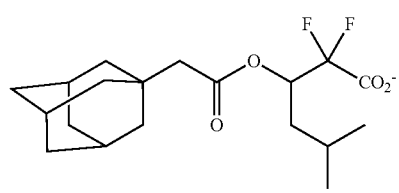 (A-34)
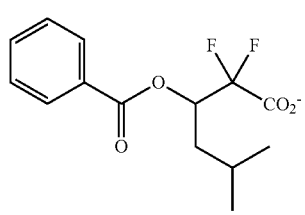 (A-35)
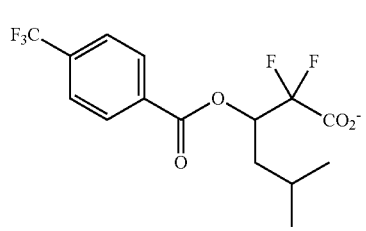 (A-36)
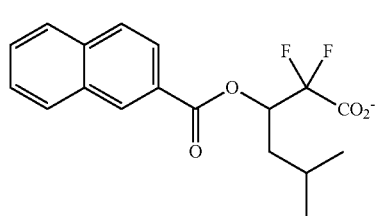 (A-37)
-continued
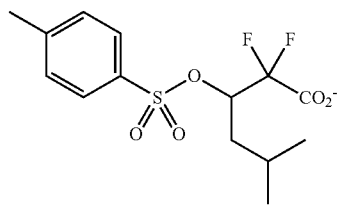 (A-38)
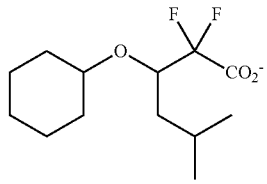 (A-39)
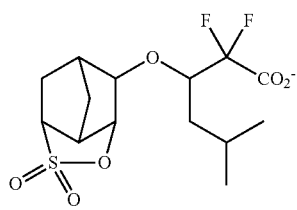 (A-40)
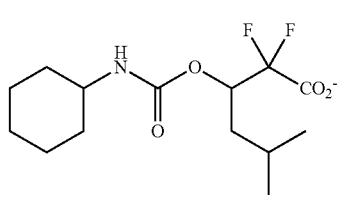 (A-41)
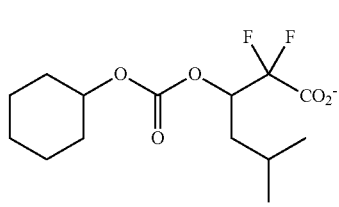 (A-42)
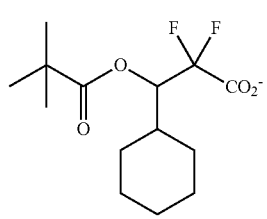 (A-43)
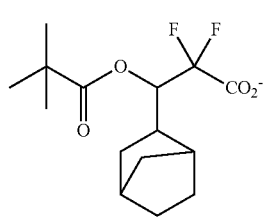 (A-44)

(A-45) 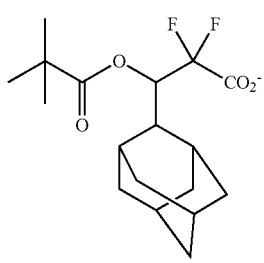

(A-46) 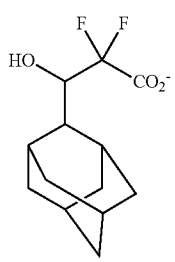

(A-47) 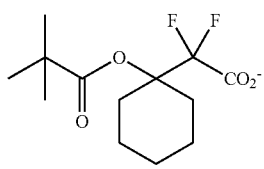

(A-48) 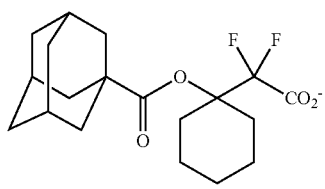

(A-49) 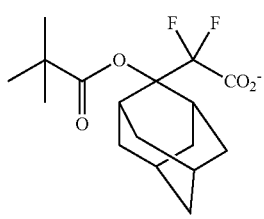

(A-50) 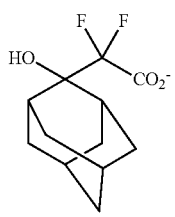

(A-51) 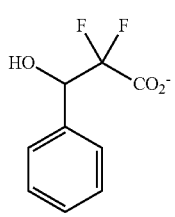

(A-52) 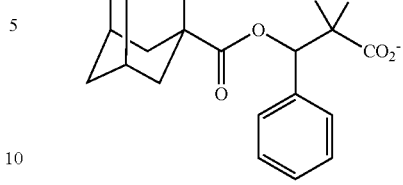

(A-53) 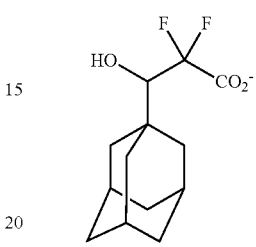

Among the above, structures (A-9) to (A-16), (A-27) to (A-34), (A-44) to (A-50), (A-52), and (A-53) are preferable anion portion of a sulfonium salt. The sulfonium salt having these structures as anion exhibits high lipid-solubility despite a carboxylate, and provides suppressed acid diffusion due to rigid structure with bicyclo ring or tricyclo ring. Therefore, such a sulfonium salt is desirable as a resist composition.

In the general formula (1), each $R^{101}$, $R^{102}$ and $R^{103}$ independently represents a linear monovalent hydrocarbon group having 1 to 20 carbon atoms or a branched or a cyclic monovalent hydrocarbon group having 3 to 20 carbon atoms with which a hetero atom may be substituted or in which a hetero atom may be included, and two or more of $R^{101}$, $R^{102}$ and $R^{103}$ may mutually be bonded to form a cyclic structure together with a sulfur atom in the formula.

Illustrative example of $R^{101}$, $R^{102}$ and $R^{103}$ includes an alkyl group such as a methyl group, an ethyl group, an n-propyl group, an isopropyl group, an n-butyl group, a tert-butyl group, a cyclopropyl group, a cyclopentyl group, a cyclohexyl group, a cyclopropylmethyl group, a 4-methylcyclohexyl group, a cyclohexylmethyl group, a norbornyl group, and an adamantyl group; an alkenyl group such as a vinyl group, an allyl group, a propenyl group, a butenyl group, a hexenyl group, and a cyclohexenyl group; an aryl group such as a phenyl group, a naphthyl group, and a thienyl group; and an aralkyl group such as a benzyl group, 1-phenylethyl group, and 2-phenylethyl group, and preferably an aryl group. Part of hydrogen atoms of these groups may be substituted with a hetero atom such as oxygen atom, sulfur atom, nitrogen atom, and halogen atom, or a hetero atom such as oxygen atom, sulfur atom, and nitrogen atom may be included. Specifically, a hydroxy group, a cyano group, a carbonyl group, an ether bond, an ester bond, a sulfonic acid ester bond, a carbonate bond, a lactone ring, a sultone ring, a carboxylic anhydride, a haloalkyl group and so on may be formed or included.

Illustrative example of a structure obtained after two of $R^{101}$, $R^{102}$ and $R^{103}$ are mutually bonded to form a cyclic structure together with a sulfur atom in the formula includes groups represented by the following formulae.

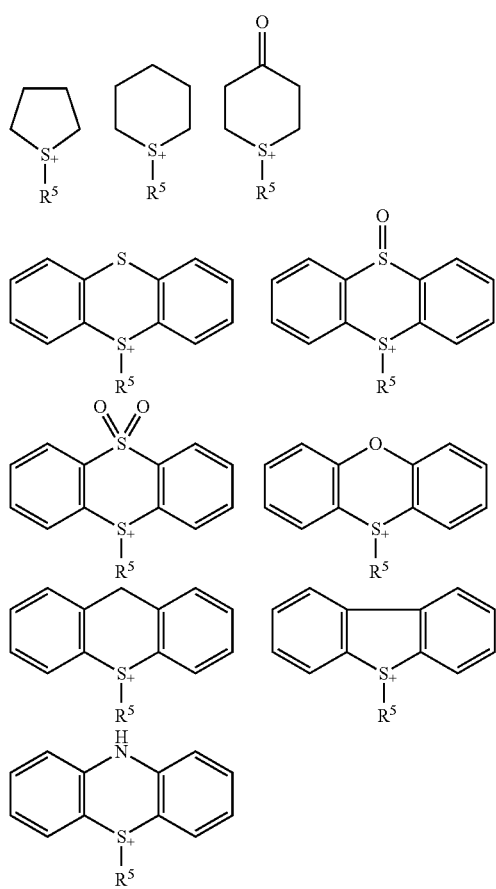
In the above formula, $R^5$ represents the same as groups illustrated as the $R^{101}$, $R^{102}$ and $R^{103}$.
Illustrative example of a structure at a cation portion of the sulfonium salt represented by the general formula (1) is shown as follows, but the present invention is not limited thereto.
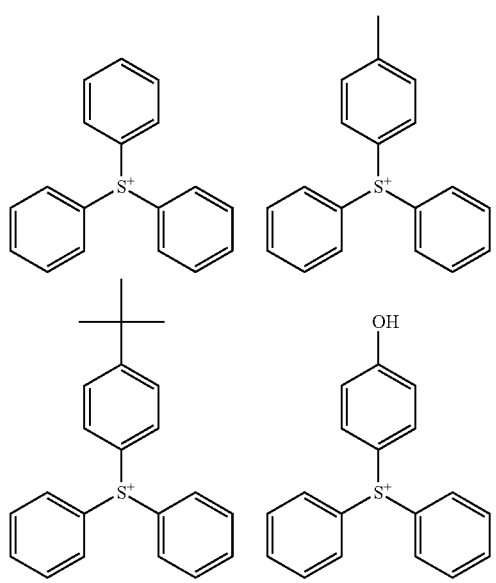
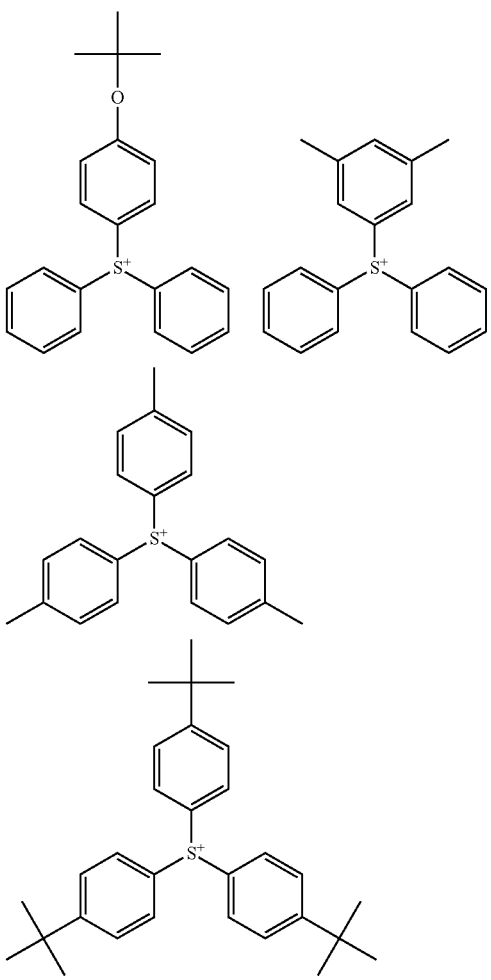

-continued

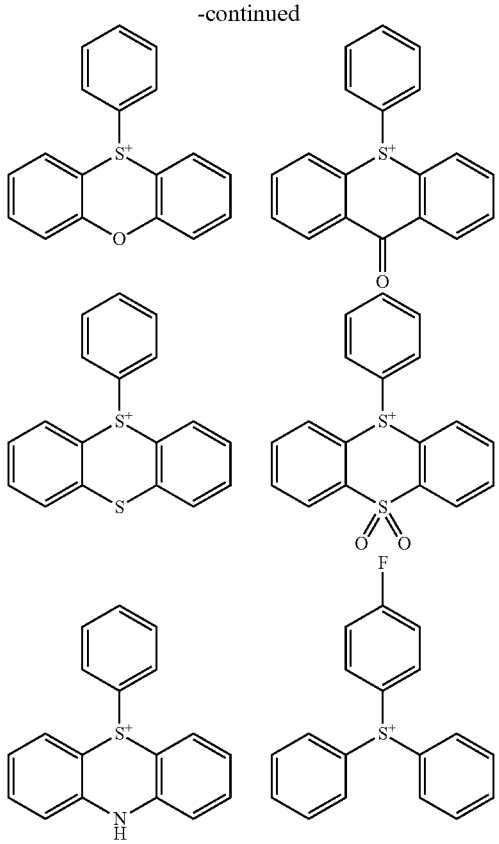

Illustrative example of a structure of the sulfonium salt of the present invention includes the ones obtained by an optional combination of the above-described anion and cation.

A resist composition containing the salt represented by the general formula (1) of the present invention generates a carboxylic acid with which a fluorine atom is substituted at α position by exposure. Since the carboxylic acid is of higher acidity than a carboxylic acid with which a fluorine atom is not substituted at α position, it can cut an acetal bond that protects a phenolic hydroxyl group of a resin in the resist composition to achieve deprotection. Additionally, a carboxylic acid with which a fluorine atom is substituted at α position generated has of lower acidity than a conventionally used alkanesulfonic acid or arenesulfonic acid. Thus, even if a carboxylic acid with which a fluorine atom is substituted at α position has diffused into a non-exposed area, an undesired cutting reaction for an acetal, which is found in a conventionally used sulfonic acid, is not likely to occur. Consequently, roughness such as LER can be reduced.

It is preferable that the acidity of a carboxylic acid generated from the salt represented by the general formula (1) (pKa) be in the range of 0.0 to 2.0, and the range of 0.2 to 1.8 is more preferable. If pKa is 0.0 or more, the carboxylic acid has an appropriate acid strength for cutting an acetal bond to obtain a pattern with reduced roughness. If pKa is 2.0 or less, the carboxylic acid has a sufficient acid strength for cutting an acetal bond.

Also, the salt represented by the general formula (1) can function as an acid diffusion control agent. A photo acid generator that generates a later-described alkanesulfonic acid or arenesulfonic acid and so on may be used in the chemically-amplified positive resist composition of the present invention. In this case, coexistence of the salt represented by the general formula (1) with the same can obtain a pattern with a lower roughness than without the same. This is attributed to an effect of the salt represented by the general formula (1) to serve as an acid diffusion control agent.

More specifically, coexistence of the salt represented by the general formula (1) and a strong acid generating onium salt that generates an acid whose acidity is relatively higher than that of an acid generated from the salt of the present invention will cause a corresponding carboxylic acid and a strong acid by photo exposure. Meanwhile, much undecomposed onium salt is found at a portion having a small exposure does. While a strong acid functions as a catalyst for causing a deprotection reaction of a base resin, a carboxylic acid generated from the salt represented by the general formula (1) hardly causes a deprotection reaction. The strong acid performs ion exchange with a residual carboxylic acid sulfonium salt, which will be turned into an onium salt of the strong acid to release a carboxylic acid instead. In other words, resulting ion exchange neutralizes the strong acid with a carboxylic acid sulfonium salt. This is probably because the carboxylic acid sulfonium salt of the present invention functions as a quencher. Normally, the onium salt-type quencher can show a lower LWR of a resist pattern than a quencher using an amine compound.

A site for a strong acid to be generated at the end of exposure is different from a site where a strong acid generating onium salt initially exists by numerously repeated salt exchange between the strong acid and the carboxylic acid sulfonium salt. It is assumed that a repeated cycle of photo acid generation and salt-exchange averages acid generation points, resulting in a smaller LWR of a resist pattern after development.

A base resin contained in the resist composition of the present invention contains a repeating unit represented by the following general formula (U-1),

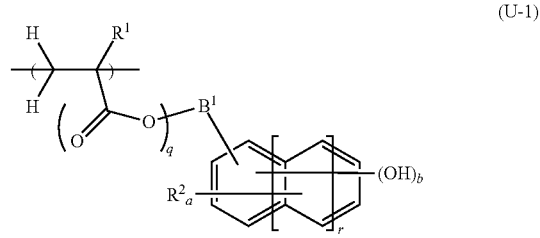

wherein "q" represents 0 or 1; "r" represents an integer of 0 to 2; $R^1$ represents any of a hydrogen atom, a fluorine atom, a methyl group, and a trifluoromethyl group; each $R^2$ independently represents a hydrogen atom or an alkyl group having 1 to 6 carbon atoms; $B^1$ represents a single bond, or an alkylene group having 1 to 10 carbon atoms that may contain an ether bond; "a" represents an integer satisfying a≤+2r−b; and "b" represents an integer of 1 to 3.

A repeating unit having no linker (—CO—O—$B^{1-}$) is a unit derived from a monomer obtained by bonding a 1-X-substituted or unsubstituted vinyl group to an aromatic ring substituted with a hydroxyl group, as typified by hydroxy styrene unit, and illustrative example of the preferable unit includes a unit derived from 3-hydroxy styrene, 4-hydroxy styrene, 5-hydroxy-2-vinylnaphthalene or 6-hydroxy-2-vinylnaphthalene.

A repeating unit having a linker (—CO—O—B$^{1-}$) is a unit derived from a vinyl monomer substituted with a carbonyl group, as typified by (meth)acrylic acid ester.
Illustrative example of the repeating unit represented by the general formula (U-1) having a linker (—CO—O—B$^{1-}$) is shown as follows.
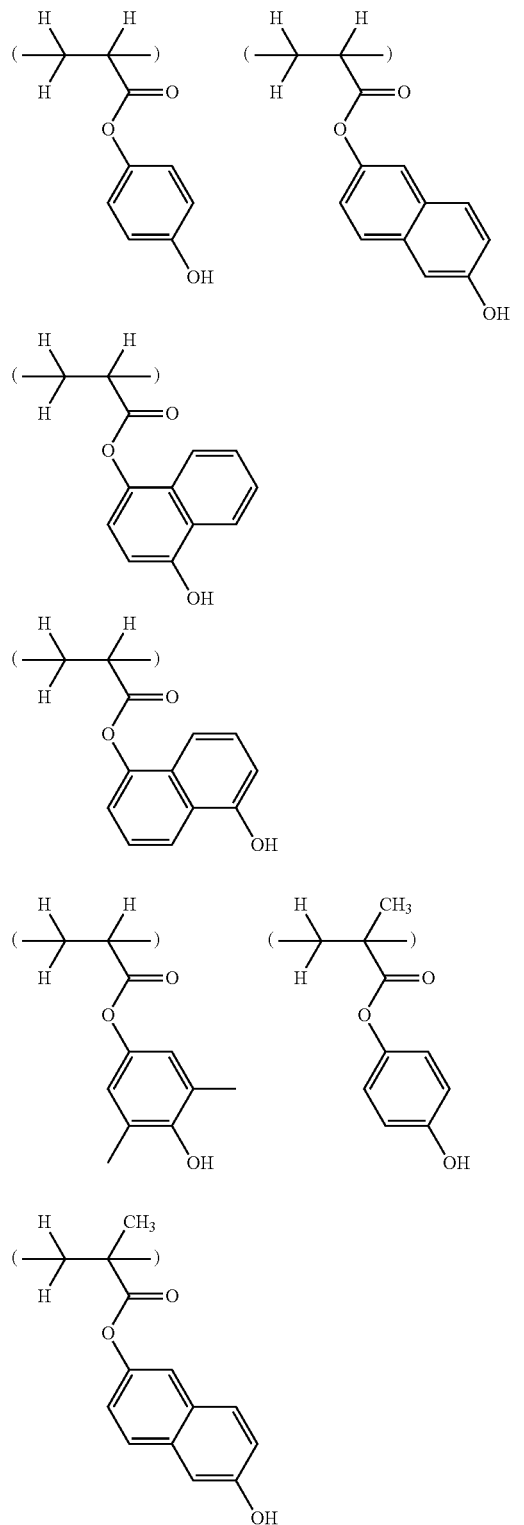
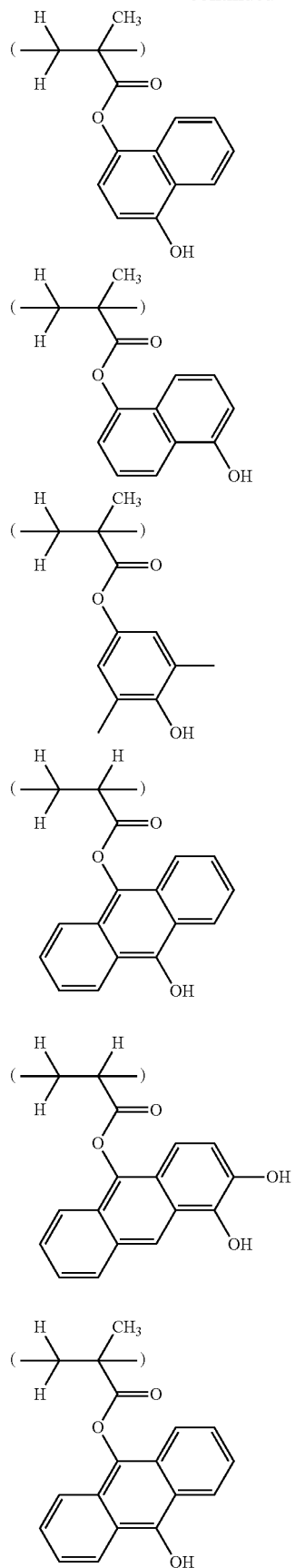

-continued

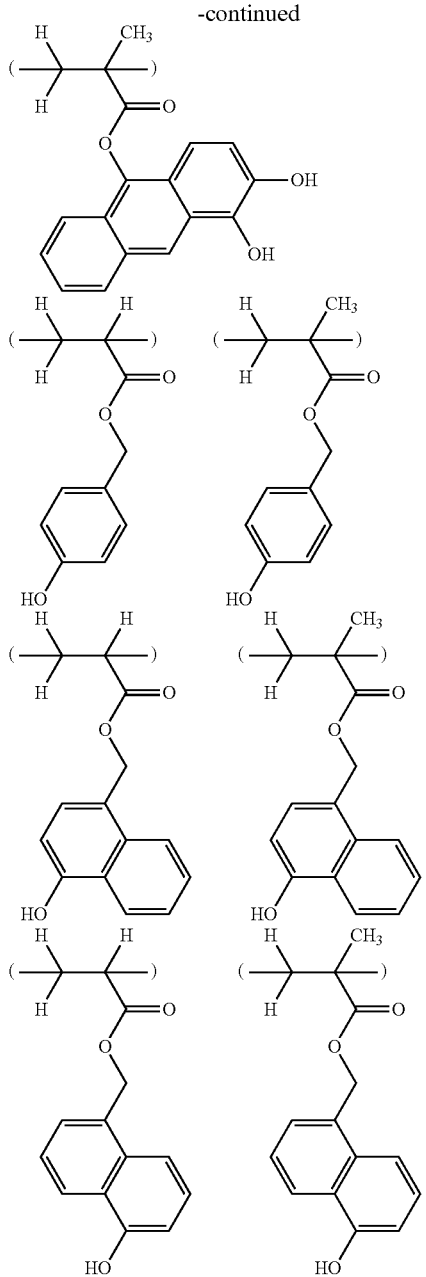

One or more unit represented by the general formula (U-1) may be used, and it is preferable that the sum of repeating units to be introduced be 40 to 90 mol %, relative to total repeating units of the base resin of the present invention. However, when at least one or more of a later-described repeating unit represented by the general formulae (U-3) and (U-4), that provides a high etching resistance to a polymer, is further contained and the unit has a phenolic hydroxyl group as a substituent, the unit is preferably used so that the total ratio is in the above range.

The resist composition of the present invention preferably contains a unit having an acid functional group protected by an acid-labile group (a unit protected by an acid-labile group to be alkali-soluble by acid action) in the base resin to be provided with a property of dissolving in an alkaline aqueous solution at exposed area, as a positive resist. Illustrative example of the most preferable unit protected by an acid-labile group to be alkali-soluble by acid action that can be contained in the polymer of the present invention includes a repeating unit represented by the following general formula (U-2),

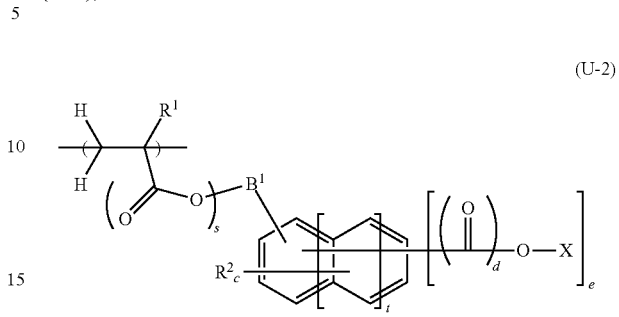

wherein "s" represents 0 or 1; "t" represents an integer of 0 to 2; $R^1$, $R^2$, and $B^1$ are the same as before; "c" represents an integer satisfying $c \leq +2t-e$; "d" represents 0 or 1; "e" represents an integer of 1 to 3; and X represents an acid labile group if "e" represents 1 and a hydrogen atom or an acid labile group if "e" represents 2 or more, but at least one thereof represents an acid labile group.

The general formula (U-2) represents the structure obtained by protecting with an acid-labile group at least one phenolic hydroxyl group with which an aromatic ring of the unit represented by the general formula (U-1) is substituted, or the structure obtained by substituting the phenolic hydroxyl group with a carboxyl group, and protecting a carboxylic acid with an acid-labile group. The acid-labile group is not particularly restricted so long as it provides an acidic group by deprotection by acid action that has already been used in many known chemically-amplified resist compositions, and any such acid-labile group can be used.

The acid-labile group, particularly a tertiary alkyl group is preferably selected to provide a pattern having low LER (a phenomenon of a pattern to show an irregular shape at an edge thereof) even if a thin resist film whose thickness is 10 to 100 nm is coated to form a fine pattern having a line width of, for example, 45 nm or less. Moreover, a tertiary alkyl group used in this case preferably has 4 to 18 carbon atoms to obtain a monomer for polymerization by distilling. Illustrative example of the alkyl substituent in a tertiary carbon of the tertiary alkyl group includes a linear, a branched or a cyclic alkyl group having 1 to 15 carbon atoms that may partially contain an oxygen-containing functional group such as an ether bond and a carbonyl group, and alkyl substituents of the tertiary carbon may be bonded to form a cyclic structure.

Illustrative example of the alkyl substituent includes a methyl group, an ethyl group, a propyl group, an adamantyl group, a norbornyl group, a tetrahydrofuran-2-yl group, a 7-oxanorbornane-2-yl group, a cyclopentyl group, a 2-tetrahydrofuryl group, a tricyclo[5.2.1.0$^{2,6}$]decyl group, a tetracyclo[4.4.0.1$^{2,5}$,1$^{7,10}$]dodecyl group, and a 3-oxo-1-cyclohexyl group. Illustrative example of the tertiary alkyl group having these as a substituent includes a t-butyl group, a t-pentyl group, a 1-ethyl-1-methylpropyl group, a 1,1-diethylpropyl group, a 1,1,2-trimethylpropyl group, a 1-adamantyl-1-methylethyl group, a 1-methyl-1-(2-norbornyl) ethyl group, a 1-methyl-1-(tetrahydrofuran-2-yl)ethyl group, a 1-methyl-1-(7-oxanorbornane-2-yl)ethyl group, a 1-methyl cyclopentyl group, a 1-ethyl cyclopentyl group, a 1-propyl cyclopentyl group, a 1-cyclopentyl cyclopentyl group, a 1-cyclohexyl cyclopentyl group, a 1-(2-tetrahydrofuryl)cyclopentyl group, a 1-(7-oxanorbornane-2-yl)cyclopentyl group, a 1-methyl cyclohexyl group, a 1-ethyl cyclohexyl group, a 1-cyclopentylcyclohexyl group, a 1-cyclohexyl cyclohexyl group, a 2-methyl-2-norbornyl group, a 2-ethyl-2-norbornyl group, a 8-methyl-8-tricyclo[5.2.1.0$^{2,6}$]decyl group, a 8-ethyl-8-tricyclo[5.2.1.0$^{2,6}$]decyl group, a 3-methyl-3-tetracyclo[4.4.0.1$^{2,5}$,1$^{7,10}$]dodecyl group, a 3-ethyl-3-tetracyclo[4.4.0.1$^{2,5}$,1$^{7,10}$]dodecyl group, a 2-methyl-2-adamantyl group, a 2-ethyl-2-adamantyl group, a 1-methyl-3-oxo-1-cyclohexyl group, a 1-methyl-1-(tetrahydrofuran-2-yl)ethyl group, a 5-hydroxy-2-methyl-2-adamantyl group, and a 5-hydroxy-2-ethyl-2-adamantyl group, but is not restricted to these.

In addition, an acetal group represented by the following general formula (U-11) is often used as an acid-labile group, and is a useful choice as an acid-labile group that stably provides a pattern whose interface with a substrate is relatively rectangular,

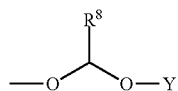
(U-11)

wherein $R^8$ represents a hydrogen atom, or a linear, a branched or a cyclic alkyl group having 1 to 10 carbon atoms; and Y represents a linear, a branched or a cyclic alkyl group having 1 to 30 carbon atoms.

The acetal group preferably contains a polycyclic alkyl group having 7 to 30 carbon atoms to obtain a higher resolution. If Y contains a polycyclic alkyl group, the acetal group preferably forms a bond between a secondary carbon comprising the polycyclic cyclic structure and an acetal oxygen. If the acetal group is bonded on the secondary carbon of a cyclic structure, the acetal group can produce a polymer-stable compound, favorable storage stability as a resist composition, and resolution does not deteriorate, compared to a case where the acetal group is bonded on a tertiary carbon. Also, the acetal group provides a favorable glass transition temperature (Tg) of a polymer, and a resist pattern after development does not cause defective shape by baking, compared to a case where Y is bonded on a primary carbon on which a linear alkyl group having one or more carbon atoms is included.

Illustrative example of the acetal group represented by the formula (U-11) is shown as follows,

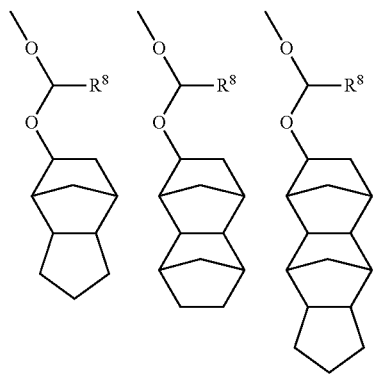

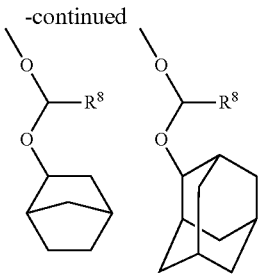
-continued wherein $R^8$ is the same as before.

In the formula, $R^8$ represents a hydrogen atom, or a linear, a branched or a cyclic alkyl group having 1 to 10 carbon atoms, and is selected according to the way sensitivity of an acid-decomposable group is designed. For instance, if a strong acid is used for decomposition while ensuring a relatively high stability, a hydrogen atom is selected, and if higher sensitivity to change in pH is achieved using a relatively high reaction, a linear alkyl group is selected. Considering a combination of an acid generator and a basic compound to be blended into a resist composition, if the end portion is substituted with a relatively large alkyl group as described above to design a large change in acid solubility by decomposition, an alkyl group in which a carbon having bond with an acetal carbon is a secondary carbon is preferably used as $R^8$. Illustrative example of $R^8$ that is bonded to the acetal carbon by the secondary carbon includes an isopropyl group, a sec-butyl group, a cyclopentyl group, and a cyclohexyl group.

Other acid-labile groups can be selected to bond a (—CH$_2$COO-tertiary alkyl group) to a phenolic hydroxyl group. The tertiary alkyl group used in this case is the-described tertiary alkyl group used in protecting a phenolic hydroxyl group.

One or more unit represented by the general formula (U-2) protected by an acid-labile group that is alkali-soluble by acid action may be used, and it is preferable that the sum of repeating units to be introduced be 5 to 45 mol %, relative to total repeating units of the base resin.

Also, the base resin preferably contains at least one or more kinds of repeating units represented by the following general formulae (U-3) and (U-4),

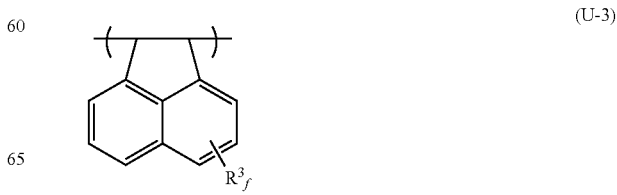
(U-3)

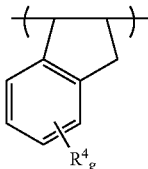

(U-4)

wherein "f" represents an integer of 0 to 6; each $R^3$ independently represents any of a hydrogen atom, an alkyl group or a primary or a secondary alkoxy group having 1 to 6 carbon atoms that may be halogen-substituted, and an alkylcarbonyloxy group having 1 to 7 carbon atoms that may be halogen-substituted; "g" represents an integer of 0 to 4; each $R^4$ independently represents any of a hydrogen atom, an alkyl or a primary or a secondary alkoxy group having 1 to 6 carbon atoms that may be halogen-substituted, and an alkylcarbonyloxy group having 1 to 7 carbon atoms that may be halogen-substituted.

When these repeating units (at least one or more kinds of repeating unit represented by the general formulae (U-3) and (U-4)) are used as a constituent, electron beam exposure resistance can be improved during etching and pattern inspection by adding a cyclic structure to a main chain, in addition to etching resistance due to an aromatic ring.

The repeating unit that provides a cyclic structure to a main chain to improve etching resistance may be used singly, or in a combination of two or more kinds. In order to improve etching resistance, it is preferable that the sum of repeating units to be introduced be 5 mol % or more, relative to total monomer units comprising the base resin. Moreover, the amount of the repeating units to be introduced, when the unit is polar by action of a functional group to provide adhesiveness to a substrate, or its substituent is protected by the acid-labile group to be alkali-soluble by acid action, is added to the-described respective ranges. When the unit has no functional group or a functional group has no action, the range is preferably 30 mol % or less. If the amount of the units to be introduced is 30 mol % or less when it has no functional group or a functional group has no action, development defect is hardly generated.

As for a base resin used in the resist composition of the present invention, as a main component unit, a unit represented by the general formulae (U-1) and (U-2), and a unit that can be introduced represented by general formulae (U-3) and (U-4) is preferably in the range of 60 mol % or more, relative to the total monomer unit in the base resin. Accordingly, an advantageous property of the resist composition of the present invention can assuredly be obtained. More preferably, the units represented by the (U-1) to (U-4) are in the range of 70 mol % or more, particularly preferably in the range of 85 mol % or more, relative to the total monomer unit.

In addition, if the total component unit is a base resin composed of repeating units selected from (U-1) to (U-4), both high etching resistance and resolution are excellently achieved. As repeating unit other than (U-1) to (U-4), (meth)acrylic acid ester unit protected with an acid labile group and (meth)acrylic acid ester unit having adhesion group such as lactone structure, which are typically used as a repeating unit, can be used. A characteristic of a resist film may be slightly adjusted by other repeating units, but the base resin may contain none of these units.

A base resin used in the resist composition of the present invention can be obtained by copolymerization of corresponding monomers in known manner, if necessary, in a combination of protection reaction and deprotection reaction. The copolymerization is not particularly restricted, but preferably radical polymerization or anion polymerization. These manners can be performed based on Japanese Patent Laid-Open Publication No. 2004-115630.

Preferably, when a molecular weight of a base resin used in the resist composition of the present invention is measured by commonly used gel permeation chromatography (GPC) using polystyrene as a standard sample, the weight average molecular weight is preferably 2,000 to 50,000, more preferably 3,000 to 20,000. If the weight average molecular weight is 2,000 or more, as conventionally known, no round T-top of a pattern is formed, resolution is not reduced and LER does not deteriorate. Meanwhile, if the molecular weight becomes larger than the required amount, LER can grow according to a pattern to be resolved. Therefore, the molecular weight is preferably 50,000 or less, and when a pattern is formed with a pattern line width of 100 nm or less, the molecular weight is particularly preferably controlled to 20,000 or less.

For GPC measurement, a commonly used tetrahydrofuran (THF) solvent can be employed.

Moreover, it is preferable that the molecular weight distribution (Mw/Mn) of the base resin to be used in the chemically-amplified resist composition of the present invention is narrow distribution in the range of 1.0 to 2.0, and particularly 1.0 to 1.8. In this case, no extraneous substances are found on a pattern after development, or a pattern profile does not deteriorate.

The resist composition of the present invention may contain a photo acid generator so that the resist composition functions as a chemically-amplified positive resist composition, or a compound that generates an acid in response to an active ray or a radiation. Any component of a photo acid generator can be used so long as it is a compound that generates an acid by high energy beam exposure. Illustrative example of a desirable photo acid generator includes sulfonium salt, iodonium salt, sulfonyl diazomethane, N-sulfonyl oxyimide, and oxime-O-sulfonate acid generator. One or more of these can be used.

Illustrative example of the photo acid generator is described in paragraphs [0122] to [0142] of Japanese Patent Laid-Open Publication No. 2008-111103.

Out of the illustrative example of the acid generator, an aryl sulfonate or alkane sulfonate photo acid generator is preferable, because it generates a properly strong acid for deprotection of an acid-labile group of the repeating unit represented by the general formula (U-2).

The resist composition of the present invention can contain a basic compound. By adding a basic compound, acid diffusion can effectively be controlled. Even if a substrate to be processed whose top surface is composed of a material containing chrome is used, the impact of an acid generated in a resist film on the material containing chrome can be reduced. The amount of the basic compound to be added is preferably 0.01 to 5 parts by mass, particularly 0.05 to 3 parts by mass, relative to 100 parts by mass of the polymer. Many known basic compounds can be used, and illustrative example thereof includes a primary, a secondary, or a tertiary aliphatic amine, a mixed amine, an aromatic amine, a heterocyclic amine, a nitrogen compound having a carboxyl group, a nitrogen compound having a sulfonyl group, a nitrogen compound having a hydroxyl group, a nitrogen compound having a hydroxyphenyl group, an alcoholic nitrogen compound, an amide, an imide, a carbamate, and an ammonium salt. Many illustrative examples of these are described in Patent Document 9, and all of these can be essentially used. In addition, 2 or more of the basic compounds can be selected and used in combination with each other.

Illustrative example of the basic compound to particularly preferably be blended includes a tris[2-(methoxymethoxy)ethyl]amine, a tris[2-(methoxymethoxy)ethyl]amine N-oxide, a morpholine derivative, and an imidazole derivative.

A surfactant conventionally used for improving the coating property on a substrate to be processed may be added to the resist composition of the present invention. When a surfactant is used, as many known examples are described in Japanese Patent Laid-Open Publication No. 2004-115630, the surfactant can be selected with reference thereto.

The amount of a surfactant to be added is preferably 2 mass parts or less, more preferably 1 mass part or less, and further preferably 0.01 mass part or more, relative to 100 mass parts of the base resin in the resist composition.

Moreover, the present invention provides a resist patterning process comprising steps of: applying the-described resist composition on a substrate to be processed to obtain a resist film; pattern-exposing by a high energy beam; and developing by using an alkaline developer.

To form a pattern by using the resist composition of the present invention, known lithography method can be employed. Generally, the resist composition is applied on a substrate to be processed such as a substrate for manufacturing an integrated circuit (Si, SiO$_2$, SiN, SiON, TiN, WSi, BPSG, SOG, organic anti-reflection film, etc.) or a substrate for manufacturing a mask circuit (Cr, CrO, CrON, MoSi, etc.) by a method such as spin-coating so that the film is 0.05 to 2.0 µm thick, and pre-baked on a heated plate at 60 to 150° C. for 1 to 20 minutes, preferably at 80 to 140° C. for 1 to 10 minutes to form a resist film.

Next, by using a mask for forming a target pattern, or directly by beam exposure, a pattern is exposed so that the exposure does of a high energy beam such as an ultraviolet ray, a far-ultraviolet ray, an excimer laser, an electron beam, an EUV, an X ray, a y ray, a synchrotron radiation is 1 to 200 mJ/cm$^2$, preferably 10 to 100 mJ/cm$^2$. The chemically-amplified resist composition of the present invention is particularly effective in pattern-exposing by an EUV or an electron beam. For exposure, normal exposure method and Immersion method for immersing between a mask and a resist can be used. In this case, a water-insoluble top coat can be used.

Subsequently, the resist composition is subjected to post exposure bake (PEB) on a heated plate at 60 to 150° C. for 1 to 20 minutes, preferably at 80 to 140° C. for 1 to 10 minutes. Furthermore, the pattern is developed for 0.1 to 3 minutes, preferably for 0.5 to 2 minutes by means of a normal method such as dip method, puddle method and spray method, using a developer of an alkaline aqueous solution such as 0.1 to 5% by mass, preferably 2 to 3% by mass of tetramethyl ammonium hydroxide (TMAH) to form a target pattern on a substrate.

The resist composition of the present invention has a particularly high etching resistance, and it is preferably used under the condition of a small change in pattern line width even if the duration until heating is extended after exposure. Also, it is particularly useful for a substrate whose surface includes a material prone to pattern peel-off or pattern collapse since adhesiveness of a resist pattern is hard to control on a substrate to be processed, and particularly useful in patterning, on a substrate obtained by subjecting a chromium metal or a chrome compound containing 1 or more light element such as oxygen, nitrogen and carbon to sputtering coating on a top surface of the substrate, particularly on a photo mask blank.

EXAMPLES

The present invention will be described with reference to the Examples and Comparative Examples, but the present invention is not restricted to the following Examples. In the following Examples, Me represents a methyl group, copolymerization composition ratio is denoted by molar ratio, and weight average molecular weight (Mw) is denoted in terms of polystyrene according to gel permeation chromatography (GPC).

Synthesis Example 1

Synthesis of Carboxylic Acid Sulfonium Salt

Carboxylic acid sulfonium salt used in the present invention is synthesized by using the following prescription.

Synthesis Example 1-1

Synthesis of 1-adamantane carboxylic acid 1-(difluoromethoxycarbonylmethyl)-2-methylpropyl ester (Intermediate 1)

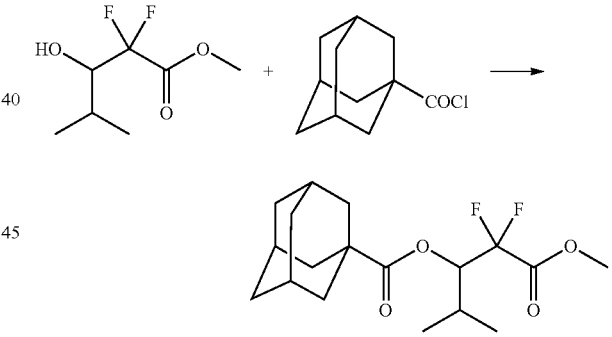

Methyl 2,2-difluoro-3-hydroxy-4-methyl pentanoate (16 g) and 1-adamantane carbonyl chloride (19 g) synthesized according to a method described in Japanese Patent Laid-Open Publication No. 2012-97256 were dissolved in methylene chloride (100 g), and a mixed solution of triethyl amine (11 g), 4-dimethyl aminopyridine (1 g) and methylene chloride (20 g) was dropped into the obtained solution under ice cooling. After aging overnight, 5% by mass of hydrochloric acid was added to the product to quench the same, then a reaction solution was washed with water, and concentrated. Methylisobutyl ketone was added to the concentrated solution to be concentrated again and the concentrated solution was distilled to obtain a target compound, or 1-adamantane carboxylic acid 1-(difluoromethoxycarbonylmethyl)-2-methylpropyl ester (20 g) as a colorless oily matter (yield: 67%).

Synthesis Example 1-2

Synthesis of triphenylsulfonium 3-(adamantane-1-carbonyloxy)-2,2-difluoro-4-methyl pentanoate (Salt-1)

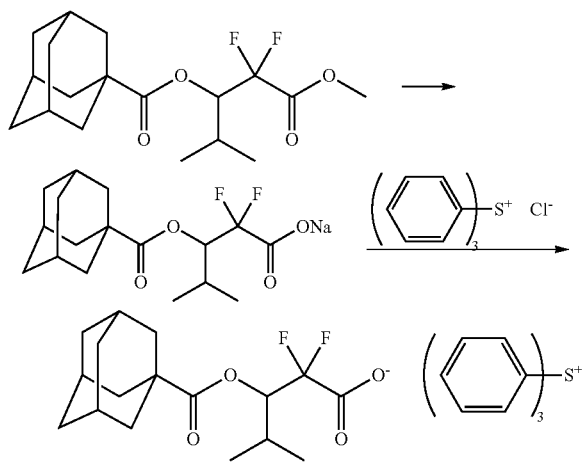

25% by mass of caustic soda (4.8 g) was added to a mixed solution of 1-adamantane carboxylic acid 1-(difluoromethoxycarbonylmethyl)-2-methylpropyl ester (10 g) prepared in Synthesis Example 1-1, 1,4-dioxane (50 g) and water (20 g), stirred for 2 hours, and then a reaction solution was washed with n-hexane to prepare an aqueous solution of sodium 3-(adamantane-1-carbonyloxy)-2,2-difluoro-4-methylpentanoate. An aqueous solution of triphenylsulfonium chloride (48 g) and methylene chloride (200 g) were added thereto, stirred for 30 minutes, and then an organic layer was isolated and washed with water, and thereafter was concentrated under reduced pressure. Methylisobutyl ketone was added to the concentrated solution to perform concentration again. Diisopropyl ether was added to the concentrated solution for crystallization, and a solid obtained was dried under reduced pressure to obtain a target compound, or triphenylsulfonium 3-(adamantane-1-carbonyloxy)-2,2-difluoro-4-methyl pentanoate (15 g) as a white crystal (yield: 86%).

Synthesis Example 1-3

Synthesis of 4-tert-butylphenyl diphenylsulfonium 3-(adamantane-1-carbonyloxy)-2,2-difluoro-4-methylpentanoate (Salt-2)

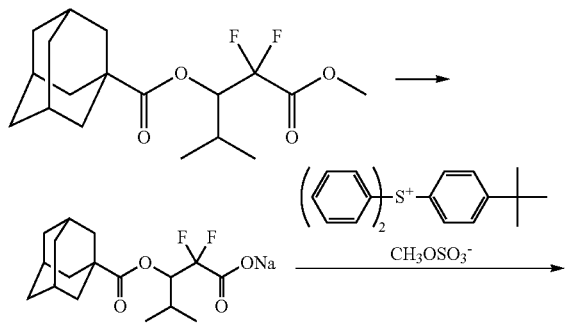

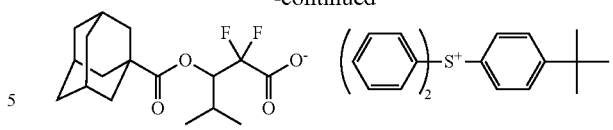

25% by mass of caustic soda (3.2 g) was added to a mixed solution of 1-adamantane carboxylic acid 1-(difluoromethoxycarbonylmethyl)-2-methyl-propyl ester (7 g) prepared in Synthesis Example 1-1, 1,4-dioxane (50 g) and water (20 g), stirred for 2 hours, and then a reaction solution was washed with n-hexane to prepare an aqueous solution of sodium 3-(adamantane-1-carbonyloxy)-2,2-difluoro-4-methylpentanoate. An aqueous solution of 4-tert-butylphenyldiphenylsulfonium methylsulfate (95 g) and methylene chloride (150 g) were added thereto, stirred for 30 minutes, and then an organic layer was isolated and washed with water, and thereafter was concentrated under reduced pressure. Methylisobutyl ketone was add to the concentrated solution, and to perform concentration again. Diisopropyl ether was added to the concentrated solution for crystallization, and a solid obtained was dried under reduced pressure to obtain a target compound, or 4-tert-butylphenyl diphenylsulfonium 3-(adamantane-1-carbonyloxy)-2,2-difluoro-4-methylpentanoate (10 g) as a white crystal (yield: 82%).

Synthesis Example 1-4

Synthesis of 10-phenyl phenoxathiinium 3-(adamantane-1-carbonyloxy)-2,2-difluoro-4-methylpentanoate (Salt-3)

The experiment was conducted according to the method of Synthesis Example 1-2, other than use of an aqueous solution of 10-phenyl phenoxathiinium chloride in place of an aqueous solution of triphenylsulfonium chloride used in Synthesis Example 1-2, to obtain a target compound, or 10-phenyl phenoxathiinium 3-(adamantane-1-carbonyloxy)-2,2-difluoro-4-methylpentanoate (15 g) as a white crystal (yield: 85%).

Synthesis Example 1-5

Synthesis of 9-phenyl dibenzothiophenium 3-(adamantane-1-carbonyloxy)-2,2-difluoro-4-methylpentanoate (Salt-4)

The experiment was conducted according to the method of Synthesis Example 1-2, other than use of an aqueous solution of 9-phenyl dibenzothiophenium, in place of an aqueous solution of triphenylsulfonium chloride used in Synthesis Example 1-2, to obtain a target compound, or 9-phenyl dibenzothiophenium 3-(adamantane-1-carbonyloxy)-2,2-difluoro-4-methylpentanoate (15 g) as a white crystal (yield: 85%).

Synthesis Example 1-6

Synthesis of ethyl 2,2-difluoro-3-hydroxy-3-phenyl propionate (Intermediate 2)

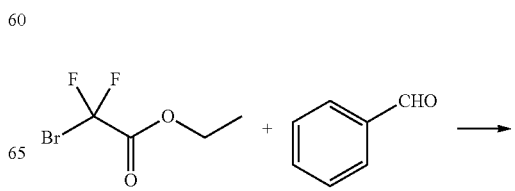

-continued

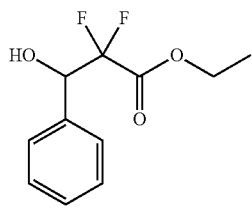

A mixed solution of ethyl bromodifluoroacetate (48 g), dibromoethane (4.5 g) and tetrahydrofuran (50 g) was dropped into a mixed solution of zinc (15 g), benzaldehyde (21 g), 60 mL of trimethyl borate and tetrahydrofuran (50 g) under heating condition of 60° C. and stirred at 90° C. for 10 hours. Thereafter, 10% by mass of hydrochloric acid (100 g) was added to the product to quench the reaction, an insoluble was removed by filtration, and a filtrate was washed with a saturated saline. The reaction solution after washing was concentrated under reduced pressure, and purified by distillation to obtain a target compound, or ethyl 2,2-difluoro-3-hydroxy-3-phenyl propionate (28 g) as a colorless oily matter (yield: 60%).

Synthesis Example 1-7

Synthesis of 1-adamantane carboxylic acid 2-ethoxycarbonyl-2,2-difluoro-1-phenyl-ethyl ester (Intermediate 3)

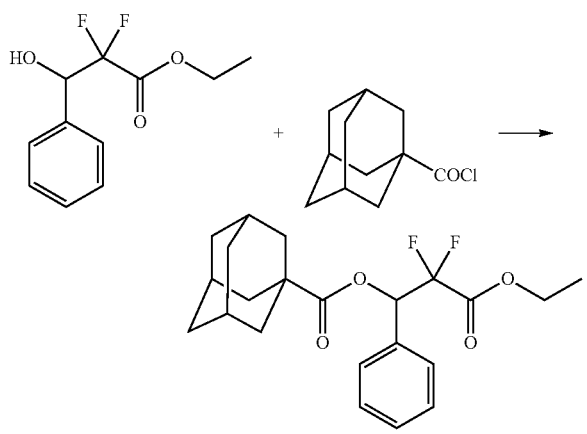

Ethyl 2,2-difluoro-3-hydroxy-3-phenylpropionate acid (9 g) prepared in Synthesis Example 1-6 and 1-adamantanecarbonyl chloride (9.5 g) were dissolved in methylene chloride (60 g), and a mixed solution of triethyl amine (6 g), 4-dimethyl aminopyridine (0.5 g) and methylene chloride (20 g) was dropped into the obtained solution under ice cooling. After aging overnight, 5% by mass hydrochloric acid was added to the product and quenched, and then the reaction solution was washed with water, and concentrated. Methylisobutyl ketone was added to the concentrated solution, and was concentrated again to obtain a target compound, or 1-adamantane carboxylic acid 2-ethoxycarbonyl-2,2-difluoro-1-phenyl-ethyl ester (15 g) as a colorless oily matter (yield: 68%).

Synthesis Example 1-8 synthesis of triphenylsulfonium 3-(adamantane-1-carbonyloxy)-2,2-difluoro-3-phenyl propionate (Salt-5)

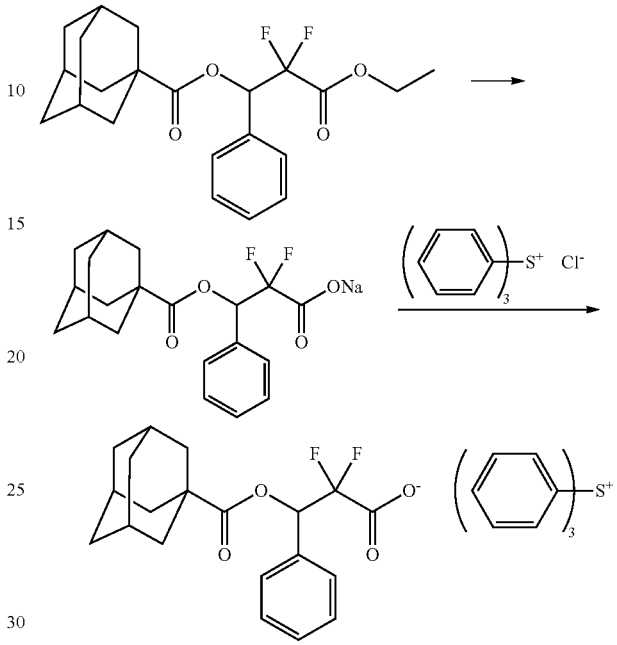

After stirring a mixed solution of 1-adamantane carboxylic acid 2-ethoxycarbonyl-2,2-difluoro-1-phenyl-ethyl ester (6.6 g) prepared in Synthesis Example 1-7, 1,4-dioxane (20 g) and 25% by mass of caustic soda (2.5 g) for 2 hours, water (30 g) was added to the reaction solution and washed with n-hexane to prepare an aqueous solution of sodium 3-(adamantane-1-carbonyloxy)-2,2-difluoro-3-phenyl propionate. An aqueous solution of triphenylsulfonium chloride (32 g) and methylene chloride (100 g) were added to the product, stirred for 30 minutes, and then an organic layer was isolated and washed with water, and thereafter was concentrated under reduced pressure. Methylisobutyl ketone was added to the concentrated solution, and concentrated again. Diisopropyl ether was added to the concentrated solution for crystallization, and a solid obtained was dried under reduced pressure to obtain a target compound, or triphenylsulfonium 3-(adamantane-1-carbonyloxy)-2,2-difluoro-3-phenyl propionate (5.5 g) as a white crystal (yield: 58%).

Synthesis Example 1-9

Synthesis of 4-tert-butylphenyl diphenyl sulfonium 3-(adamantane-1-carbonyloxy)-2,2-difluoro-3-phenyl propionate (Salt-6)

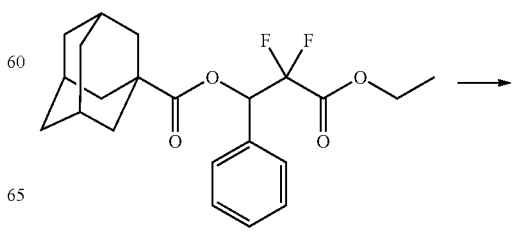

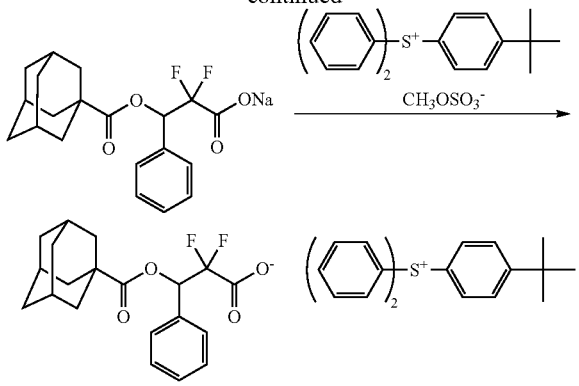
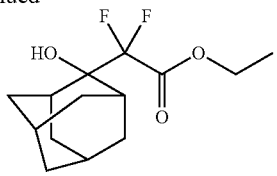

After stirring a mixed solution of 1-adamantane carboxylic acid 2-ethoxycarbonyl-2,2-difluoro-1-phenyl-ethyl ester (6.6 g) prepared in Synthesis Example 1-7, 1-4-dioxane (20 g) and 25% by mass of caustic soda (2.5 g) for 2 hours, water (30 g) was added to the reaction solution and washed with n-hexane to prepare an aqueous solution of sodium 3-(adamantane-1-carbonyloxy)-2,2-difluoro-3-phenyl propionate. An aqueous solution of 4-tert-butyl phenyldiphenylsulfonium methyl sulfate (95 g) and methylene chloride (100 g) were added to the product, stirred for 30 minutes, and then an organic layer was isolated and washed with water, and thereafter was concentrated under reduced pressure. Methylisobutyl ketone was added to the concentrated solution, and concentrated again. Diisopropyl ether was added to the concentrated solution for crystallization, and a solid obtained was dried under reduced pressure to obtain a target compound, or 4-tert-butylphenyldiphenyl sulfonium 3-(adamantane-1-carbonyloxy)-2,2-difluoro-3-phenyl propionate (5.4 g) as a white crystal (yield: 52%).

Synthesis Example 1-10

Synthesis of 10-phenyl phenoxathiinium 3-(adamantane-1-carbonyloxy)-2,2-difluoro-3-phenyl propionate (Salt-7)

The experiment was conducted according to the method of Synthesis Example 1-8, other than use of an aqueous solution of 10-phenyl phenoxathiinium chloride in place of an aqueous solution of triphenyl sulfonium chloride used in Synthesis Example 1-8, to obtain a target compound, or 10-phenyl phenoxathiinium 3-(adamantane-1-carbonyloxy)-2,2-difluoro-3-phenyl propionate (5.5 g) as a white crystal (yield: 83%).

Synthesis Example 1-11

Synthesis of ethyl difluoro-(2-hydroxyadamantane-2-yl) acetate (Intermediate 4)

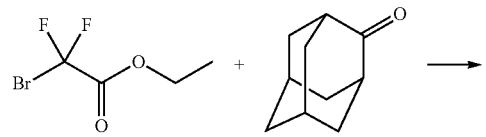

A mixed solution of ethyl bromodifluoro acetate (24 g), dibromoethane (2.2 g) and tetrahydrofuran (25 g) was dropped into a mixed solution of zinc (7.8 g), 2-adamantanone (15 g), 30 mL of trimethyl borate and tetrahydrofuran (25 g) under heating condition of 50° C. and then stirred at 80° C. for 10 hours. Thereafter, 5% by mass hydrochloric acid (50 g) was added to the product to quench the reaction, ethyl acetate (200 g) was added thereto to extract an organic layer, and the organic layer was washed with saturated saline, subsequently with water. The reaction solution washed was concentrated under reduced pressure, methylisobutyl ketone was added to the concentrated solution, and was concentrated under reduced pressure again, n-hexane was added to the concentrated solution for crystallization, and a solid obtained was dried under reduced pressure to obtain a target compound, or ethyl difluoro-(2-hydroxyadamantane-2-yl) acetate (15 g) as a white crystal (yield: 58%).

Synthesis Example 1-12

Synthesis of triphenylsulfonium difluoro-(2-hydroxyadamantane-2-yl) acetate (Salt-8)

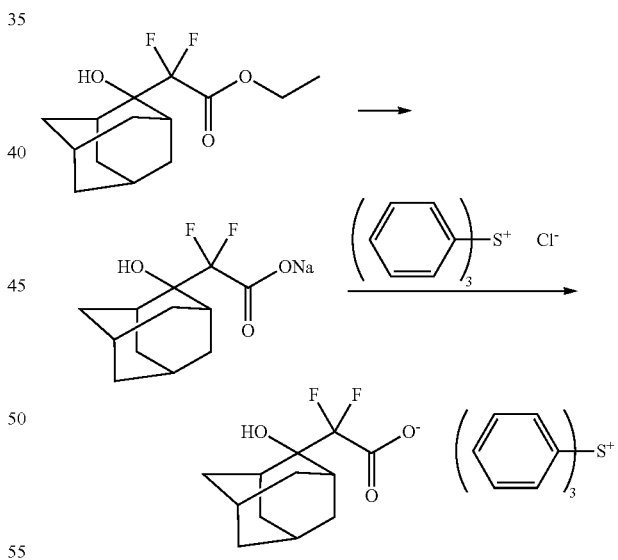

After stirring a mixed solution of ethyl difluoro-(2-hydroxyadamantane-2-yl) acetate (3.9 g) prepared in Synthesis Example 1-11, 1,4-dioxane (20 g) and 25% by mass of caustic soda (4.8 g) for 2 hours, 35% by mass hydrochloric acid (1.5 g) was added to the reaction solution, and then an aqueous solution of triphenyl sulfonium chloride (24 g) and methylene chloride (100 g) were added to the product. After stirring the product for 30 minutes, an organic layer was isolated and washed with water, and thereafter was concentrated under reduced pressure. Methylisobutyl ketone was added to the concentrated solution, and concentrated again.

Diisopropyl ether was added to the concentrated solution for crystallization, and a solid obtained was dried under reduced pressure to obtain a target compound, or triphenyl sulfonium difluoro-(2-hydroxyadamantane-2-yl) acetate (4.7 g) as a white crystal (yield: 63%).

Synthesis Example 1-13

Synthesis of 4-fluorophenyl diphenylsulfonium difluoro-(2-hydroxyadamantane-2-yl) acetate (Salt-9)

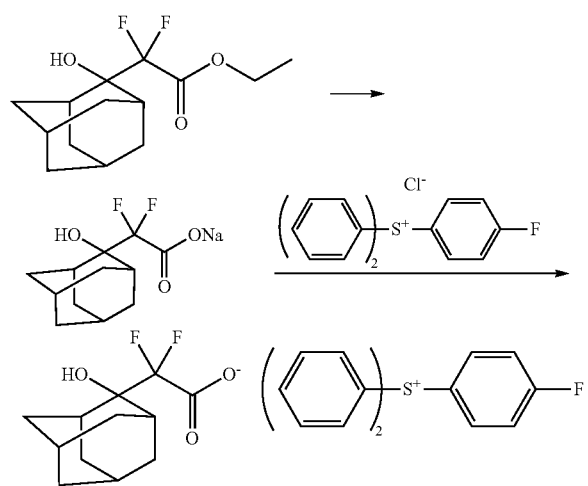

After stirring a mixed solution of ethyl difluoro-(2-hydroxyadamantane-2-yl) acetate (2.6 g) prepared in Synthesis Example 1-11, 1,4-dioxane (30 g), 25% by mass of caustic soda (4.0 g) and water (10 g) for 2 hours, 35% by mass hydrochloric acid (1.0 g) was added to the reaction solution, and an aqueous solution of 4-fluoro phenyldiphenylsulfonium chloride (66 g) and methylene chloride (100 g) were added to the product. After stirring the product for 30 minutes, an organic layer was isolated and washed with water, and thereafter was concentrated under reduced pressure. Methylisobutyl ketone was added to the concentrated solution, and concentrated again. Diisopropyl ether was added to the concentrated solution for removal of a supernatant to obtain a target compound, or 4-fluorophenyldiphenyl sulfonium difluoro-(2-hydroxyadamantane-2-yl) acetate (2.4 g) as a glassy solid (yield: 45%).

Synthesis Example 2

Synthesis of Polymer

Polymers used in the resist composition of the present invention was synthesized according to the following prescription. The composition ratio of each polymer synthesized is shown in Table 1, and the structures of repeating units are shown in Tables 2 to 4.

Polymer Synthesis Example 2-1

Synthesis of Polymer 1

Acetoxystyrene (407.5 g), acenaphthylene (42.5 g) and toluene (1275 g) as a solvent were added to a 3 L flask. The reaction vessel was cooled down to −70° C. in nitrogen atmosphere, and vacuuming under reduced pressure and nitrogen flow were repeated three times. After the temperature was raised up to room temperature, 2,2'-azobis(2,4-dimethylvaleronitrile) (Product from Wako Pure Chemical Industries, Ltd.: V-65) (34.7 g) was added to the product as a polymerization initiator, and after the temperature was further raised to 55° C., it was reacted for 40 hours. The reaction solution was agitated and a mixed solution of methanol (970 g) and water (180 g) was dropped thereinto while stirring, and 30 minutes later, a lower layer (polymer layer) was concentrated under reduced pressure. The polymer layer was dissolved again in 0.45 L of methanol and 0.54 L of tetrahydrofuran, triethyl amine (160 g) and water (30 g) were added, heated at 60° C., and was subjected to a deprotection reaction for 40 hours. The deprotection reaction solution was concentrated under reduced pressure, and methanol (548 g) and acetone (112 g) were added thereto to make a solution. Herein, hexane (990 g) was dropped thereinto while stirring, and 30 minutes later, tetrahydrofuran (300 g) was added to a lower layer (polymer layer). Herein, hexane (1030 g) was dropped thereinto while stirring, and 30 minutes later, the lower layer (polymer layer) was concentrated under reduced pressure. The polymer solution was neutralized with acetic acid (82 g) to concentrate the reaction solution. Thereafter, the product was dissolved in 0.3 L of acetone to be precipitated in 10 L of water, filtered and dried to obtain a white polymer (280 g). The obtained polymer was subjected to $^1$H-NMR and GPC measurement to obtain the following results.

Copolymerization composition ratio
  hydroxystyrene:acenaphthylene=89.3:10.7
Weight average molecular weight (Mw)=5000
Molecular weight distribution (Mw/Mn)=1.63

(2-methyl-1-propenyl)methyl ether (50 g) was reacted with the obtained polymer (100 g) under acid condition, and was subjected to steps of neutralization, separation, and crystallization to obtain a polymer 1. (yield: 125 g)

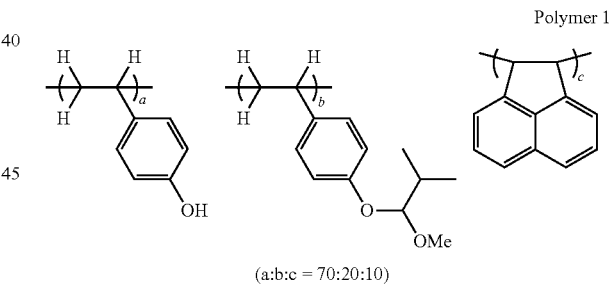

(a:b:c = 70:20:10)

Polymer 1

Polymer Synthesis Example 2-2

Synthesis of Polymer 2

The synthesis was conducted according to the method of Polymer Synthesis Example 2-1, other than use of (2-methyl-1-propenyl)-8-tricyclo[5,2,1,0$^{2,6}$]decanyl ether in place of (2-methyl-1-propenyl)methyl ether used in Polymer Synthesis Example 2-1 to obtain a polymer 2.

Polymer Synthesis Example 2-3

Synthesis of Polymer 3

The synthesis was conducted according to the method of Polymer Synthesis Example 2-1, other than use of (2-methyl-1-propenyl)-2-adamantyl ether in place of (2-methyl-1-propenyl)methyl ether used in Polymer Synthesis Example 2-1 to obtain a polymer 3.

Polymer Synthesis Example 2-4

Synthesis of Polymer 4

4-hydroxyphenyl methacrylate (362 g), acenaphthylene (38.2 g), dimethyl-2,2'-azobis(2-methyl propionate) (=V-601) (40.9 g), methylethyl ketone (500 g) were fed into a dropping cylinder in nitrogen atmosphere to prepare a monomer solution. Methylethyl ketone (250 g) was fed into another flask for polymerization in nitrogen atmosphere, stirred and heated up to 80° C., and the monomer solution was dropped thereinto for 4 hours. After completion of dropping, the temperature of a polymer solution was maintained at 80° C. and stirred for 4 hours, and then cooled down to room temperature. A polymer solution obtained was dropped into hexane/diisopropyl ether solution (10 kg) to filter off a extracted copolymer. The copolymer was washed with hexane (5 kg) twice and vacuum-dried at 50° C. for 20 hours to obtain a white powdered solid polymer. (2-methyl-1-propenyl)methyl ether (40.5 g) was reacted with a polymer (100 g) obtained under acid condition and subjected to steps of neutralization, separation, and crystallization to obtain a polymer 4. (yield: 128 g)

Polymer Synthesis Example 2-5

Synthesis of Polymer 5

The synthesis was conducted according to the method of Polymer Synthesis Example 2-4, other than use of (2-methyl-1-propenyl)-8-(tricyclo[5,2,1,0$^{2,6}$]decanyl ether in place of (2-methyl-1-propenyl)methyl ether used in Polymer Synthesis Example 2-4 to obtain a polymer 5.

Polymer Synthesis Example 2-6

Synthesis of Polymer 6

The synthesis was conducted according to the method of Polymer Synthesis Example 2-4, other than use of 2-methyl-1-propenyl)-2-adamantyl ether in place of (2-methyl-1-propenyl)methyl ether used in Polymer Synthesis Example 2-4 to obtain a polymer 6.

Polymer Synthesis Example 2-7 to 2-12

Synthesis of Polymers 7 to 12

As for a polymer containing a hydroxy styrene unit, the synthesis was conducted according to the method of Polymer Synthesis Examples 2-1, 2-2 and 2-3 by using different types and blending ratios of each monomer to produce polymers shown in Table 1. Also, as for a polymer containing a 4-hydroxyphenyl methacrylate unit, the synthesis was conducted according to the method of Polymer Synthesis Examples 2-4, 2-5 and 2-6 by using different types and blending ratios of each monomer to produce polymers shown in Table 1.

Polymer Synthesis Example 2-13

Synthesis of Polymer 13

4-hydroxyphenyl methacrylate (42.4 g), 5-oxo-4-oxatricyclo[4.2.1.0$^{3,7}$]nonane-2-yl methacrylate (40.6 g), 1-methoxy-2-methyl-1-propyl methacrylate (16.9 g), dimethyl-2,2'-azobis(2-methyl propionate)(V-601) (9.3 g) and methylethyl ketone (124 g) were fed into a dropping cylinder in nitrogen atmosphere to prepare a monomer solution. Methylethyl ketone (62 g) was fed into another flask for polymerization in nitrogen atmosphere, stirred and heated up to 80° C., and thereafter the monomer solution was dropped for 4 hours. After completion of dropping, the temperature of a polymer solution was maintained at 80° C. and stirred for 4 hours, and then cooled down to room temperature. A polymer solution obtained was dropped into a hexane/diisopropyl ether solution (1.5 kg) to filter off a extracted copolymer. After the copolymer was washed with hexane (300 g) twice, it was vacuum-dried at 50° C. for 20 hours to obtain a white powdered solid polymer.

Polymer Synthesis Example 2-14, 15, 16

Synthesis of Polymers 14, 15 and 16

The synthesis was conducted according to the method of Polymer Synthesis Example 2-13 by using different types and blending ratios of each monomer to produce resins shown in Table 1.

The structures of each unit in Table 1 are shown in Tables 2 to 4. In the following Table 1, the introduction ratio is denoted by molar ratio.

TABLE 1

| | Unit 1 | Introduction ratio (mol %) | Unit 2 | Introduction ratio (mol %) | Unit 3 | Introduction ratio (mol %) |
|---|---|---|---|---|---|---|
| Polymer 1 | A-1 | 70.0 | B-1 | 20.0 | C-1 | 10.0 |
| Polymer 2 | A-1 | 78.0 | B-3 | 12.0 | C-1 | 10.0 |
| Polymer 3 | A-1 | 79.0 | B-5 | 11.0 | C-1 | 10.0 |
| Polymer 4 | A-2 | 67.0 | B-2 | 23.0 | C-1 | 10.0 |
| Polymer 5 | A-2 | 76.0 | B-4 | 14.0 | C-1 | 10.0 |
| Polymer 6 | A-2 | 77.0 | B-6 | 13.0 | C-1 | 10.0 |
| Polymer 7 | A-1 | 68.0 | B-1 | 22.0 | C-2 | 10.0 |
| Polymer 8 | A-1 | 76.0 | B-3 | 14.0 | C-2 | 10.0 |
| Polymer 9 | A-1 | 77.0 | B-5 | 13.0 | C-2 | 10.0 |
| Polymer 10 | A-2 | 64.0 | B-2 | 26.0 | C-2 | 10.0 |
| Polymer 11 | A-2 | 73.0 | B-4 | 17.0 | C-2 | 10.0 |
| Polymer 12 | A-2 | 74.0 | B-6 | 16.0 | C-2 | 10.0 |
| Polymer 13 | A-2 | 46.0 | B-7 | 19.0 | C-3 | 35.0 |
| Polymer 14 | A-2 | 50.0 | B-8 | 15.0 | C-3 | 35.0 |
| Polymer 15 | A-2 | 50.0 | B-9 | 15.0 | C-3 | 35.0 |
| Polymer 16 | A-1 | 67.0 | B-10 | 23.0 | C-1 | 10.0 |

TABLE 2

A-1

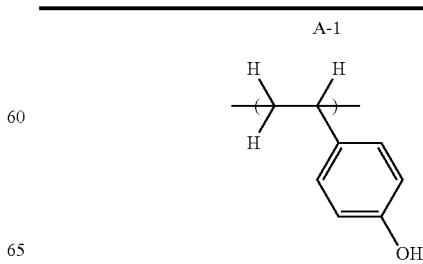

TABLE 2-continued
A-2
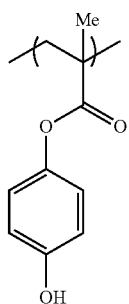
TABLE 3
B-1
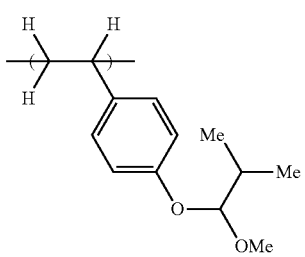 [SMILES: CCC(C)c1ccc(OC(OC)C(C)C)cc1]
B-2
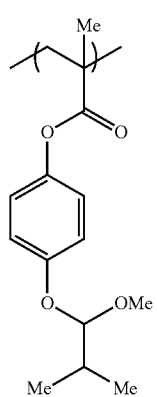
B-3
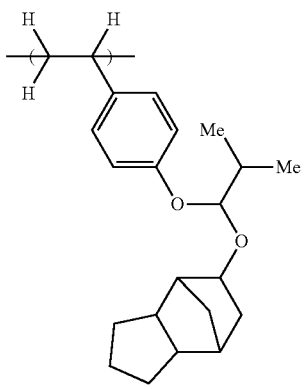 [SMILES: CCC(C)c1ccc(OC(OC2CC3CC2C2CCCC32)C(C)C)cc1]
TABLE 3-continued
B-4
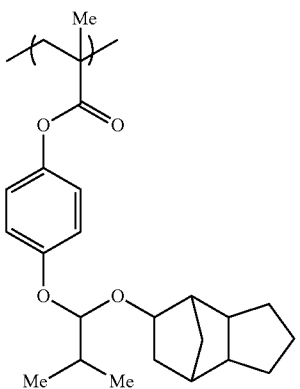
B-5
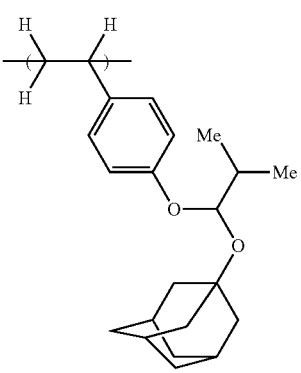 [SMILES: CCC(C)c1ccc(OC(OC23CC4CC(CC(C4)C2)C3)C(C)C)cc1]
B-6
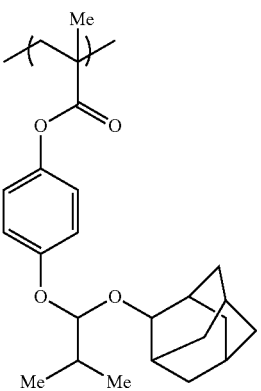
B-7
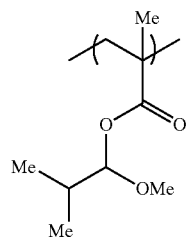

TABLE 3-continued

B-8

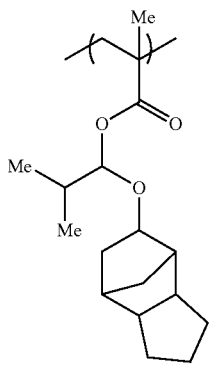

B-9

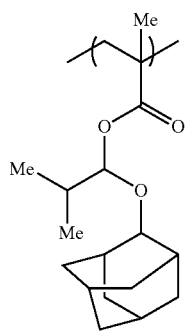

B-10

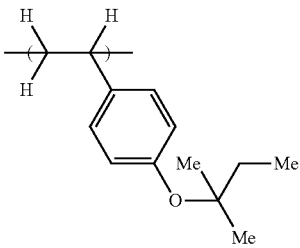 [SMILES: CCC(C)c1ccc(OC(C)(C)CC)cc1]

TABLE 4

C-1

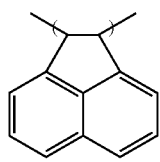

C-2

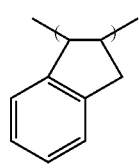

TABLE 4-continued

C-3

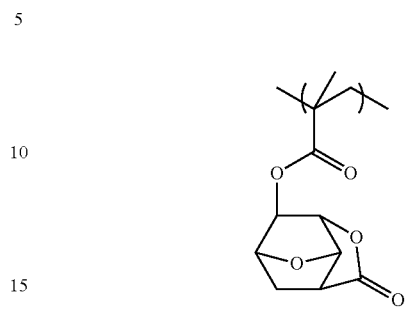

Preparation of Positive Resist Composition (1)

(A) a salt of the present invention synthesized above as a photo acid generator, or a comparative salt, (B) polymers synthesized above (polymers 1 to 16), and (C) an acid diffusion control agent, the components were dissolved in an organic solvent by using compositions shown in Table 6 to prepare a resist composition. Each composition was filtered by using a filter 0.2 μm thick or a nylon or an UPE filter 0.02 μm thick to prepare a solution of a positive resist composition. The acid diffusion control agent used has structures represented by the following Base-1 and Base-2. The structures of the salt of the present invention and comparative salt used are shown in the following Table 5. The organic solvents shown in Table 6 are PGMEA (propylene glycol monomethyl etheracetate), EL (ethyl lactate), PGME (propylene glycol monomethyl ether), or CyH (cyclohexanone). Also, as a surfactant, 0.075 parts by mass of PF-636 (Product from OMNOVA SOLUTIONS Inc.) was added to each composition.

(Base-1)

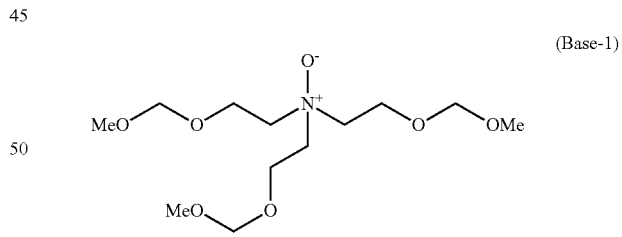

(Base-2)

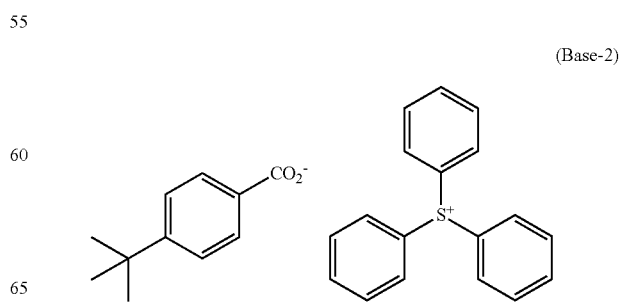

TABLE 5
Salt-1
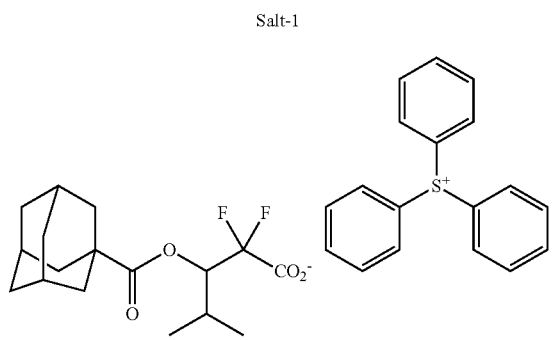
Salt-2
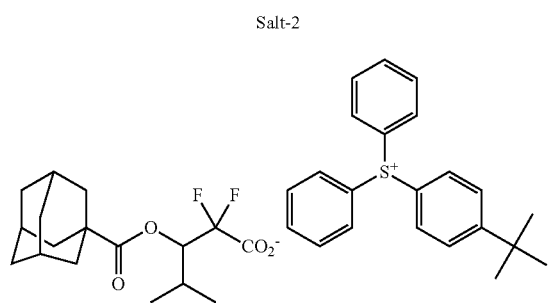
Salt-3
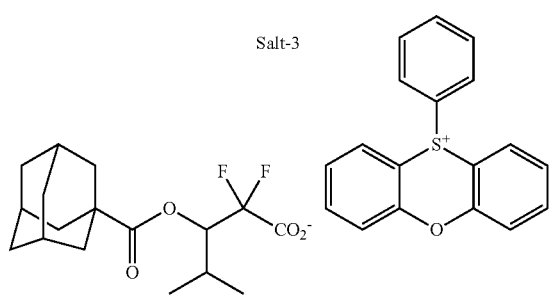
Salt-4
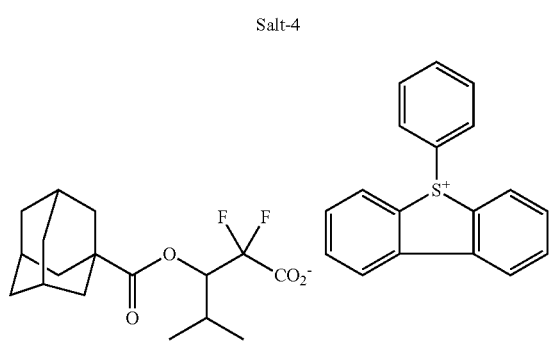
Salt-5
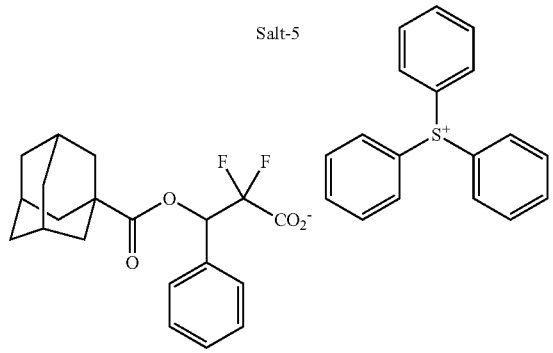
TABLE 5-continued
Salt-6
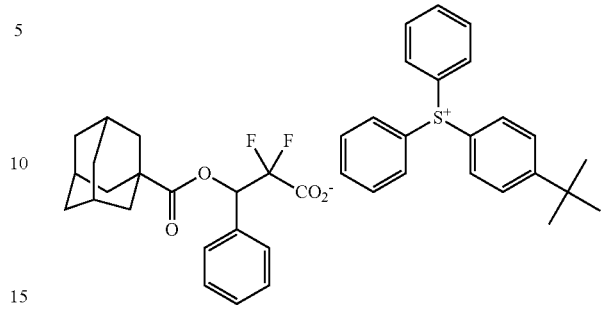
Salt-7
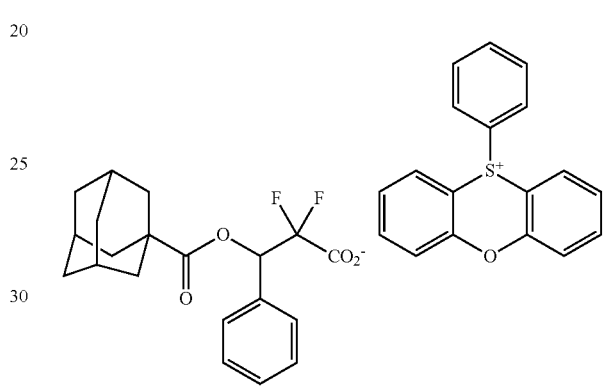
Salt-8
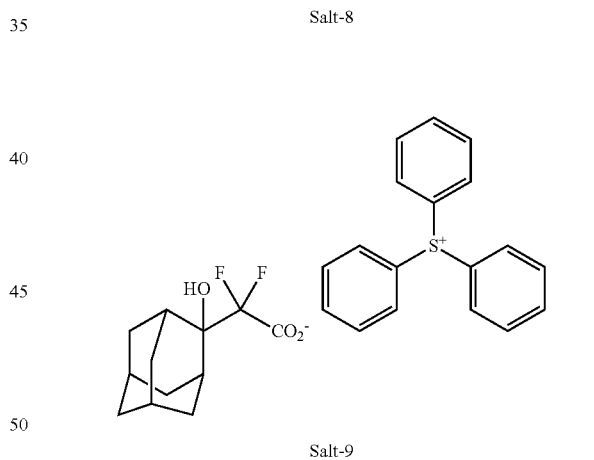
Salt-9
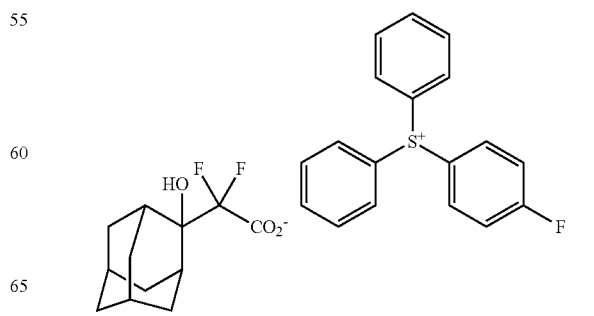

TABLE 5-continued comparative salt-1

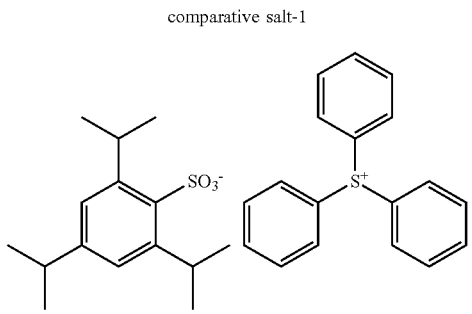

comparative salt-2

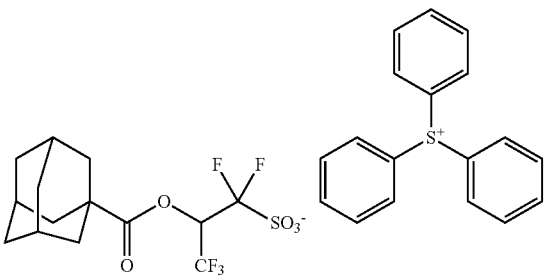

TABLE 6

| | Photo acid generator | Resin | Acid diffusion control agent | Solvent 1 | Solvent 2 | Solvent 3 |
|---|---|---|---|---|---|---|
| Example 1 | Salt-1 (8) | Polymer 1 (80) | Base-1 (0.9) | PGMEA (1,000) | EL (1,000) | PGME (1,300) |
| Example 2 | Salt-1 (8) | Polymer 2 (80) | Base-1 (1.1) | PGMEA (1,000) | EL (1,000) | PGME (1,300) |
| Example 3 | Salt-1 (10) | Polymer 2 (80) | Base-1 (1.4) | PGMEA (1,000) | EL (1,000) | PGME (1,300) |
| Example 4 | Salt-1 (12) | Polymer 2 (80) | Base-1 (1.7) | PGMEA (1,000) | EL (1,000) | PGME (1,300) |
| Example 5 | Salt-1 (8) | Polymer 3 (80) | Base-1 (1.1) | PGMEA (1,000) | EL (1,000) | PGME (1,300) |
| Example 6 | Salt-1 (10) | Polymer 3 (80) | Base-1 (1.4) | PGMEA (1,000) | EL (1,000) | PGME (1,300) |
| Example 7 | Salt-1 (12) | Polymer 3 (80) | Base-1 (1.7) | PGMEA (1,000) | EL (1,000) | PGME (1,300) |
| Example 8 | Salt-1 (8) | Polymer 2 (80) | Base-2 (1.8) | PGMEA (1,000) | EL (1,000) | PGME (1,300) |
| Example 9 | Salt-1 (10) | Polymer 2 (80) | Base-2 (2.3) | PGMEA (1,000) | EL (1,000) | PGME (1,300) |
| Example 10 | Salt-1 (12) | Polymer 2 (80) | Base-2 (2.5) | PGMEA (1,000) | EL (1,000) | PGME (1,300) |
| Example 11 | Salt-1 (8) | Polymer 3 (80) | Base-2 (1.8) | PGMEA (1,000) | EL (1,000) | PGME (1,300) |
| Example 12 | Salt-1 (10) | Polymer 3 (80) | Base-2 (2.3) | PGMEA (1,000) | EL (1,000) | PGME (1,300) |
| Example 13 | Salt-1 (12) | Polymer 3 (80) | Base-2 (2.5) | PGMEA (1,000) | EL (1,000) | PGME (1,300) |
| Example 14 | Salt-1 (8) | Polymer 4 (80) | Base-1 (1.5) | PGMEA (1,000) | EL (1,000) | PGME (1,300) |
| Example 15 | Salt-1 (8) | Polymer 5 (80) | Base-1 (1.5) | PGMEA (1,000) | EL (1,000) | PGME (1,300) |
| Example 16 | Salt-1 (8) | Polymer 6 (80) | Base-1 (1.3) | PGMEA (1,000) | EL (1,000) | PGME (1,300) |
| Example 17 | Salt-1 (8) | Polymer 7 (80) | Base-1 (1.6) | PGMEA (1,000) | EL (1,000) | PGME (1,300) |
| Example 18 | Salt-1 (8) | Polymer 8 (80) | Base-1 (1.1) | PGMEA (1,000) | EL (1,000) | PGME (1,300) |
| Example 19 | Salt-1 (8) | Polymer 9 (80) | Base-1 (1.4) | PGMEA (1,000) | EL (1,000) | PGME (1,300) |
| Example 20 | Salt-1 (8) | Polymer 10 (80) | Base-1 (1.3) | PGMEA (1,000) | EL (1,000) | PGME (1,300) |
| Example 21 | Salt-1 (8) | Polymer 11 (80) | Base-1 (1.6) | PGMEA (1,000) | EL (1,000) | PGME (1,300) |
| Example 22 | Salt-1 (8) | Polymer 12 (80) | Base-1 (1.1) | PGMEA (1,000) | EL (1,000) | PGME (1,300) |
| Example 23 | Salt-1 (4) Salt-2 (6) | Polymer 2 (80) | Base-1 (1.4) | PGMEA (1,000) | EL (1,000) | PGME (1,300) |
| Example 24 | Salt-3 (4) Salt-2 (6) | Polymer 2 (80) | Base-1 (1.4) | PGMEA (1,000) | EL (1,000) | PGME (1,300) |
| Example 25 | Salt-4 (4) Salt-2 (6) | Polymer 2 (80) | Base-1 (1.4) | PGMEA (1,000) | EL (1,000) | PGME (1,300) |
| Example 26 | Salt-5 (4) Salt-6 (5) | Polymer 2 (80) | Base-1 (1.8) | PGMEA (1,000) | EL (1,000) | PGME (1,300) |
| Example 27 | Salt-7 (5) Salt-6 (5) | Polymer 2 (80) | Base-1 (1.8) | PGMEA (1,000) | EL (1,000) | PGME (1,300) |
| Example 28 | Salt-8 (5) Salt-9 (5) | Polymer 2 (80) | Base-1 (1.6) | PGMEA (1,000) | EL (1,000) | PGME (1,300) |
| Example 29 | Salt-3 (8) | Polymer 2 (80) | Base-1 (1.8) | PGMEA (1,000) | EL (1,000) | PGME (1,300) |
| Example 30 | Salt-4 (8) | Polymer 2 (80) | Base-1 (1.9) | PGMEA (1,000) | EL (1,000) | PGME (1,300) |
| Example 31 | Salt-2 (8) | Polymer 3 (80) | Base-1 (1.3) | PGMEA (1,000) | EL (1,000) | PGME (1,300) |
| Example 32 | Salt-3 (8) | Polymer 3 (80) | Base-1 (1.7) | PGMEA (1,000) | EL (1,000) | PGME (1,300) |
| Example 33 | Salt-4 (8) | Polymer 3 (80) | Base-1 (1.6) | PGMEA (1,000) | EL (1,000) | PGME (1,300) |
| Example 34 | Salt-5 (8) | Polymer 3 (80) | Base-1 (1.5) | PGMEA (1,000) | EL (1,000) | PGME (1,300) |
| Example 35 | Salt-6 (8) | Polymer 3 (80) | Base-1 (1.5) | PGMEA (1,000) | EL (1,000) | PGME (1,300) |
| Example 36 | Salt-7 (8) | Polymer 3 (80) | Base-1 (1.5) | PGMEA (1,000) | EL (1,000) | PGME (1,300) |
| Example 37 | Salt-8 (8) | Polymer 3 (80) | Base-1 (1.4) | PGMEA (1,000) | EL (1,000) | PGME (1,300) |
| Example 38 | Salt-9 (8) | Polymer 3 (80) | Base-1 (1.5) | PGMEA (1,000) | EL (1,000) | PGME (1,300) |
| Example 39 | Salt-5 (8) | Polymer 8 (80) | Base-1 (1.8) | PGMEA (1,000) | EL (1,000) | PGME (1,300) |
| Example 40 | Salt-5 (8) | Polymer 9 (80) | Base-1 (1.9) | PGMEA (1,000) | EL (1,000) | PGME (1,300) |
| Example 41 | Salt-6 (8) | Polymer 8 (80) | Base-1 (1.8) | PGMEA (1,000) | EL (1,000) | PGME (1,300) |
| Example 42 | Salt-6 (8) | Polymer 9 (80) | Base-1 (1.9) | PGMEA (1,000) | EL (1,000) | PGME (1,300) |
| Example 43 | Salt-8 (8) | Polymer 8 (80) | Base-1 (1.5) | PGMEA (1,000) | EL (1,000) | PGME (1,300) |
| Example 44 | Salt-9 (8) | Polymer 9 (80) | Base-1 (1.5) | PGMEA (1,000) | EL (1,000) | PGME (1,300) |
| Example 45 | Salt-1 (8) | Polymer 13 (80) | Base-1 (1.4) | PGMEA (800) | CyH (1,600) | PGME (400) |
| Example 46 | Salt-1 (8) | Polymer 14 (80) | Base-1 (1.5) | PGMEA (800) | CyH (1,600) | PGME (400) |
| Example 47 | Salt-1 (8) | Polymer 15 (80) | Base-1 (1.3) | PGMEA (800) | CyH (1,600) | PGME (400) |
| Example 48 | Salt-1 (8) | Polymer 16 (80) | Base-1 (1.5) | PGMEA (1,000) | EL (1,000) | PGME (1,300) |
| Comparative | Comparative | Polymer 2 (80) | Base-1 (1.0) | PGMEA (1,000) | EL (1,000) | PGME (1,300) |

TABLE 6-continued

| | Photo acid generator | Resin | Acid diffusion control agent | Solvent 1 | Solvent 2 | Solvent 3 |
|---|---|---|---|---|---|---|
| Example 1 | Salt-1 (8) | | | | | |
| Comparative Example 2 | Comparative Salt-1 (10) | Polymer 2 (80) | Base-1 (1.0) | PGMEA (1,000) | EL (1,000) | PGME (1,300) |
| Comparative Example 3 | Comparative Salt-1 (8) | Polymer 3 (80) | Base-1 (1.0) | PGMEA (1,000) | EL (1,000) | PGME (1,300) |
| Comparative Example 4 | Comparative Salt-1 (10) | Polymer 3 (80) | Base-1 (1.0) | PGMEA (1,000) | EL (1,000) | PGME (1,300) |
| Comparative Example 5 | Comparative Salt-2 (8) | Polymer 2 (80) | Base-1 (4.0) | PGMEA (1,000) | EL (1,000) | PGME (1,300) |
| Comparative Example 6 | Comparative Salt-2 (8) | Polymer 13 (80) | Base-1 (4.1) | PGMEA (800) | CyH (1,600) | PGME (400) |

The resist composition s of the present invention (Examples 1 to 48) shown in the Table 6 contain a resin containing an acetal group and a salt represented by the general formula (1). The salt represented by the general formula (1) in these resist compositions functions as a photo acid generator when the temperature of a later-described PEB is 120° C.

Electron Beam Lithography Evaluation (1)
(Examples 1 to 44, 48, Comparative Examples 1 to 5)

The positive resist compositions prepared above (Examples 1 to 44, 48, Comparative Examples 1 to 5) were spin-coated on a mask blank whose 152 mm square top surface is a chrome oxynitride film using an ACT-M (Product from Tokyo Electron Limited), and pre-baked on a heated plate at 90° C. for 600 seconds to produce a resist film 90 nm thick. The film thickness of a resist film obtained was measured using optical instrument nanospec (Product from Nanometrics Incorporated). The film thickness was measured at 81 in-plate positions of a blank substrate other than an outer edge portion within 10 mm from a blank outer circumference to calculate the average film thickness value and the ranges of the film thickness.

Moreover, each product was exposed using an electron beam exposure apparatus (Product from NuFlare Technology Inc.: EBM-5000plus, accelerating voltage; 50 keV), and baked (PEB: post exposure bake) at 120° C. for 600 seconds. The development was conducted using an aqueous solution of 2.38% by mass of tetra methyl ammonium hydroxide to obtain a positive pattern. A resist pattern obtained was evaluated as follows.

A patterned mask blank produced was observed with top-down scanning electron microscope (SEM), the exposure does for resolving 400 nm 1:1 line and space (LS) by 1:1 was defined as an optimal exposure does ($\mu C/cm^2$), and the minimum dimension at the exposure does for resolving 400 nm 1:1 line and space (LS) by 1:1 was defined as limiting resolution, and a 200 nm LS edge roughness (LER) was measured with SEM. It was visually determined whether the pattern shape is rectangular or not. To evaluate CDU (CD uniformity), the line width, subjected to the exposure does ($\mu C/cm^2$) for resolving a 400 nm 1:1 line and space by 1:1, was measured at 49 in-plate positions of a blank substrate other than an outer edge portion within 20 mm from a blank outer circumference to calculate $3\sigma$ value from a value obtained by deducting a measuring point from its average line width value. Each resist composition was evaluated and the results are shown in Table 7.

TABLE 7

| | Optimum exposure ($\mu C/cm^2$) | Limiting resolution (nm) | LER (nm) | CDU($3\sigma$) (nm) | Pattern shape |
|---|---|---|---|---|---|
| Example 1 | 21 | 45 | 4.7 | 2.1 | Rectangular |
| Example 2 | 24 | 40 | 4.8 | 2.5 | Rectangular |
| Example 3 | 25 | 40 | 4.5 | 2.1 | Rectangular |
| Example 4 | 21 | 45 | 4.9 | 2.5 | Rectangular |
| Example 5 | 25 | 45 | 4.7 | 2.5 | Rectangular |
| Example 6 | 20 | 45 | 4.9 | 2.5 | Rectangular |
| Example 7 | 24 | 40 | 4.5 | 2.2 | Rectangular |
| Example 8 | 20 | 45 | 4.5 | 2.6 | Rectangular |
| Example 9 | 24 | 40 | 4.5 | 2.4 | Rectangular |
| Example 10 | 22 | 45 | 4.9 | 2.6 | Rectangular |
| Example 11 | 21 | 45 | 4.8 | 2.2 | Rectangular |
| Example 12 | 21 | 45 | 4.9 | 2.3 | Rectangular |
| Example 13 | 25 | 40 | 5.0 | 2.4 | Rectangular |
| Example 14 | 23 | 45 | 5.0 | 2.2 | Rectangular |
| Example 15 | 20 | 40 | 4.8 | 2.1 | Rectangular |
| Example 16 | 22 | 45 | 4.8 | 2.2 | Rectangular |
| Example 17 | 21 | 40 | 4.8 | 2.2 | Rectangular |
| Example 18 | 24 | 40 | 4.6 | 2.4 | Rectangular |
| Example 19 | 23 | 45 | 4.7 | 2.4 | Rectangular |
| Example 20 | 25 | 45 | 4.9 | 2.4 | Rectangular |
| Example 21 | 25 | 40 | 4.6 | 2.6 | Rectangular |
| Example 22 | 20 | 40 | 4.5 | 2.3 | Rectangular |
| Example 23 | 20 | 45 | 4.8 | 2.6 | Rectangular |
| Example 24 | 23 | 45 | 4.7 | 2.5 | Rectangular |
| Example 25 | 24 | 40 | 4.5 | 2.4 | Rectangular |
| Example 26 | 23 | 45 | 4.6 | 2.3 | Rectangular |
| Example 27 | 23 | 40 | 4.8 | 2.5 | Rectangular |
| Example 28 | 24 | 45 | 4.6 | 2.5 | Rectangular |
| Example 29 | 25 | 40 | 4.7 | 2.3 | Rectangular |
| Example 30 | 22 | 45 | 4.8 | 2.4 | Rectangular |
| Example 31 | 23 | 45 | 4.6 | 2.6 | Rectangular |
| Example 32 | 23 | 40 | 4.7 | 2.5 | Rectangular |
| Example 33 | 22 | 45 | 4.5 | 2.5 | Rectangular |
| Example 34 | 25 | 40 | 4.9 | 2.6 | Rectangular |
| Example 35 | 23 | 45 | 4.8 | 2.4 | Rectangular |
| Example 36 | 24 | 45 | 4.8 | 2.5 | Rectangular |
| Example 37 | 24 | 45 | 4.7 | 2.4 | Rectangular |
| Example 38 | 23 | 40 | 4.8 | 2.5 | Rectangular |
| Example 39 | 24 | 40 | 4.9 | 2.5 | Rectangular |
| Example 40 | 23 | 45 | 4.7 | 2.4 | Rectangular |
| Example 41 | 21 | 45 | 4.6 | 2.5 | Rectangular |
| Example 42 | 24 | 45 | 4.7 | 2.5 | Rectangular |
| Example 43 | 24 | 45 | 4.6 | 2.5 | Rectangular |
| Example 44 | 23 | 45 | 4.8 | 2.3 | Rectangular |
| Example 48 | 25 | 40 | 4.7 | 2.6 | Rectangular |
| Comparative Example 1 | 24 | 50 | 5.7 | 3.4 | Rectangular |
| Comparative Example 2 | 23 | 45 | 5.9 | 3.5 | Rectangular |
| Comparative Example 3 | 25 | 50 | 6.1 | 3.6 | Rectangular |

TABLE 7-continued

|  | Optimum exposure (μC/cm²) | Limiting resolution (nm) | LER (nm) | CDU(3σ) (nm) | Pattern shape |
|---|---|---|---|---|---|
| Comparative Example 4 | 26 | 50 | 5.8 | 3.6 | Rectangular |
| Comparative Example 5 | 26 | 80 | 8.4 | 4.3 | Tapered |

EUV Exposure Evaluation (1) (Examples 45 to 47, Comparative Example 6

The positive resist compositions prepared above (Examples 45 to 47, Comparative Example 6) were spin-coated on an Si substrate of 4 inch in diameter treated with vapor prime with hexamethyldisilazane (HMDS) and pre-baked on a heated plate at 105° C. for 60 seconds to produce a resist film 50 nm thick. The product was subjected to EUV exposure by using NA 0.3 dipole illumination.

Just after exposure, the product was subjected to post exposure bake (PEB) on a heated plate for 60 seconds, puddle-developed for 30 seconds by using 2.38% by mass of a TMAH aqueous solution to obtain a positive pattern.

A resist pattern obtained was evaluated as follows. The minimum dimension at the exposure does for resolving 35 nm line and space (LS) by 1:1 was defined as a limiting resolution to measure a 35 nm LS line edge roughness (LER) with SEM. It was visually determined whether the pattern shape is rectangular or not. Each resist composition was evaluated and the results are shown in Table 8.

TABLE 8

|  | Optimum exposure (mJ/cm²) | Limiting resolution (nm) | LER (nm) | Pattern shape |
|---|---|---|---|---|
| Example 45 | 15 | 28 | 4.0 | Rectangular |
| Example 46 | 14 | 30 | 4.1 | Rectangular |
| Example 47 | 14 | 28 | 4.3 | Rectangular |
| Comparative Example 6 | 12 | 50 | 7.5 | Tapered |

The results in the Tables 7 and 8 will be described. In the Tables 7 and 8, the salt represented by the general formula (1) is used as a photo acid generator. The resist compositions containing the salt represented by the general formula (1) of the present invention (Examples 1 to 44, 48 and Examples 45 to 47) all showed favorable resolution and favorable pattern rectangular property, and LER was also a favorable value. Meanwhile, resist compositions in Comparative Examples 1 to 5 and 6 by using a salt that generates benzenesulfonic acid or fluorinated alkanesulfonic acid as an acid generator by exposure showed unfavorable resolution, LER and CDU, compared to Examples. This is attributed to an undesirable reaction: slight deprotection of a protective group in a base resin at a non-exposed area as a result of acid diffusion generated by exposure to a non-exposed area. Since resist compositions containing the salt of the present invention have a lower acidity than resist compositions containing a salt used in Comparative Examples, the undesirable reaction is not relatively likely to occur, compared to resist compositions using a salt of Comparative Examples. Consequently, a pattern having reduced roughness can be formed.

Preparation of Positive Resist Composition (2)

(A) a salt of the present invention synthesized above as an acid diffusion control agent, or a comparative salt,
(B) polymers (polymers 1 to 16) synthesized above, and
(C) a salt of a structure represented by the following PAG-1 to PAG-4 as a photo acid generator,
the components were dissolved in an organic solvent by using compositions shown in Table 10 to prepare a resist composition. Each composition was filtered with a filter 0.2 μm thick or a nylon or an UPE filter 0.02 μm thick to prepare each solution of positive resist compositions. The organic solvent in Table 10 was PGMEA (propylene glycol monomethyl etheracetate), EL (ethyl lactate), PGME (propylene glycol monomethyl ether), or CyH (cyclohexanone). Also, as a surfactant, 0.075 parts by mass PF-636 (Product from OMNOVA SOLUTIONS) was added to each composition. In addition, the structures of the salt of the present invention used and comparative salts are shown in the following Table 9.

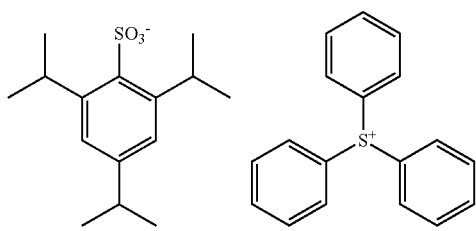

(PAG-1)

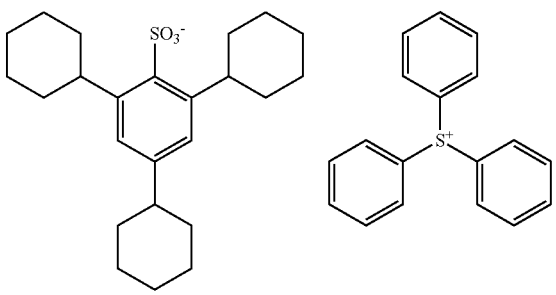

(PAG-2)

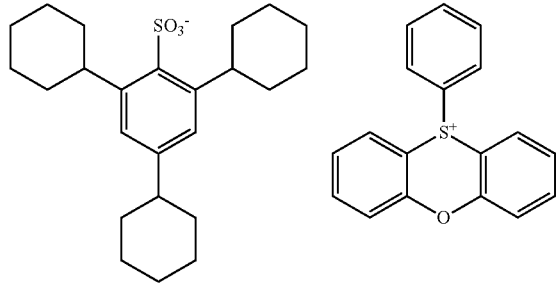
(PAG-3)
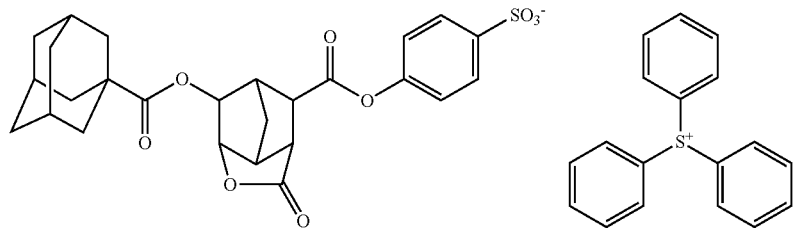
(PAG-4)
| TABLE 9 | TABLE 9-continued |
| --- | --- |
| Salt-1 | Salt-5 |
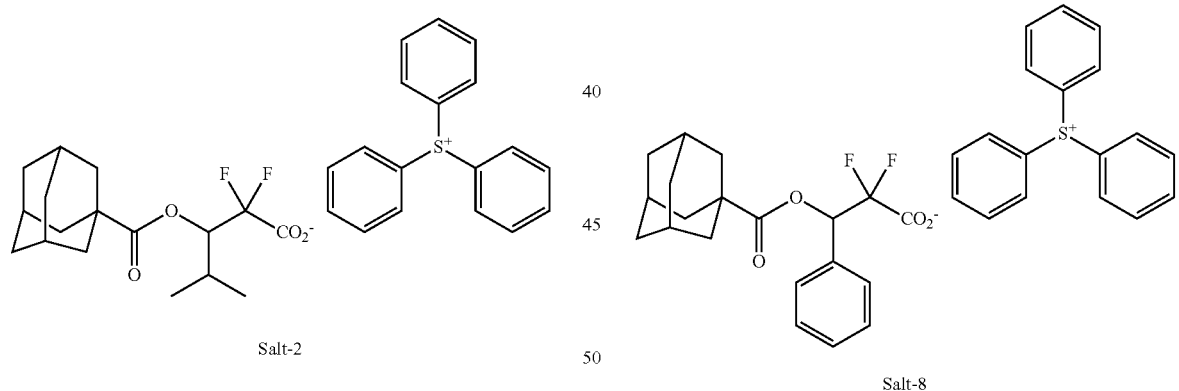
Salt-2
Salt-8
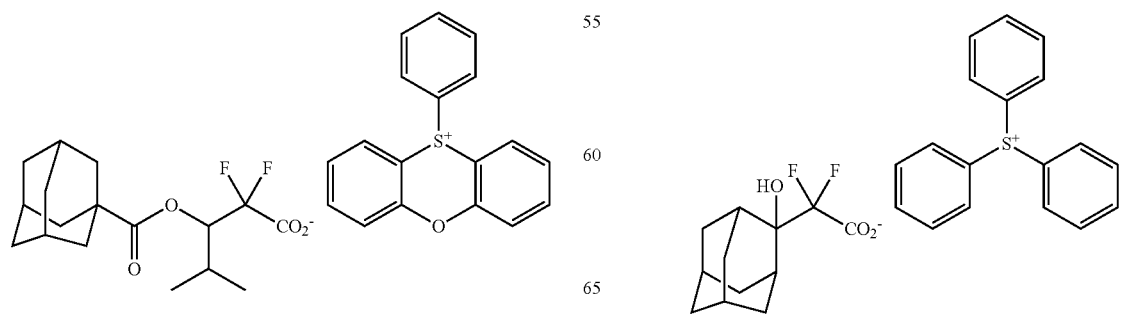

TABLE 9-continued comparative salt-3

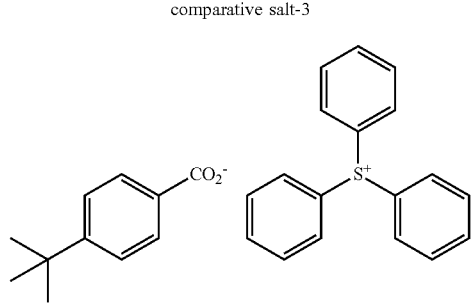

comparative salt-4

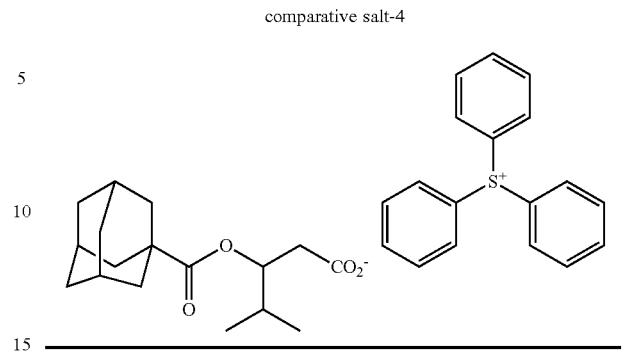

TABLE 10

|  | Acid diffusion control agent | Resin | Photo acid generator | Solvent 1 | Solvent 2 | Solvent 3 |
|---|---|---|---|---|---|---|
| Example 49 | Salt-1 (5.0) | Polymer 1 (80) | PAG-1 (8) | PGMEA (1,000) | EL (1,000) | PGME (1,300) |
| Example 50 | Salt-1 (5.0) | Polymer 2 (80) | PAG-1 (8) | PGMEA (1,000) | EL (1,000) | PGME (1,300) |
| Example 51 | Salt-1 (5.5) | Polymer 2 (80) | PAG-1 (10) | PGMEA (1,000) | EL (1,000) | PGME (1,300) |
| Example 52 | Salt-1 (5.4) | Polymer 2 (80) | PAG-2 (10) | PGMEA (1,000) | EL (1,000) | PGME (1,300) |
| Example 53 | Salt-1 (5.3) | Polymer 2 (80) | PAG-3 (10) | PGMEA (1,000) | EL (1,000) | PGME (1,300) |
| Example 54 | Salt-1 (5.3) | Polymer 2 (80) | PAG-2 (5) PAG-3 (5) | PGMEA (1,000) | EL (1,000) | PGME (1,300) |
| Example 55 | Salt-1 (5.3) | Polymer 2 (80) | PAG-4 (10) | PGMEA (1,000) | EL (1,000) | PGME (1,300) |
| Example 56 | Salt-1 (7.3) | Polymer 2 (80) | PAG-1 (12) | PGMEA (1,000) | EL (1,000) | PGME (1,300) |
| Example 57 | Salt-1 (7.2) | Polymer 2 (80) | PAG-2 (12) | PGMEA (1,000) | EL (1,000) | PGME (1,300) |
| Example 58 | Salt-1 (7.2) | Polymer 2 (80) | PAG-4 (12) | PGMEA (1,000) | EL (1,000) | PGME (1,300) |
| Example 59 | Salt-1 (5.2) | Polymer 3 (80) | PAG-1 (8) | PGMEA (1,000) | EL (1,000) | PGME (1,300) |
| Example 60 | Salt-1 (5.8) | Polymer 3 (80) | PAG-1 (10) | PGMEA (1,000) | EL (1,000) | PGME (1,300) |
| Example 61 | Salt-1 (5.7) | Polymer 3 (80) | PAG-2 (10) | PGMEA (1,000) | EL (1,000) | PGME (1,300) |
| Example 62 | Salt-1 (5.6) | Polymer 3 (80) | PAG-3 (10) | PGMEA (1,000) | EL (1,000) | PGME (1,300) |
| Example 63 | Salt-1 (5.6) | Polymer 3 (80) | PAG-2 (5) PAG-3 (5) | PGMEA (1,000) | EL (1,000) | PGME (1,300) |
| Example 64 | Salt-1 (7.6) | Polymer 3 (80) | PAG-1 (12) | PGMEA (1,000) | EL (1,000) | PGME (1,300) |
| Example 65 | Salt-1 (7.6) | Polymer 3 (80) | PAG-2 (12) | PGMEA (1,000) | EL (1,000) | PGME (1,300) |
| Example 66 | Salt-1 (7.8) | Polymer 3 (80) | PAG-3 (12) | PGMEA (1,000) | EL (1,000) | PGME (1,300) |
| Example 67 | Salt-1 (5.2) | Polymer 4 (80) | PAG-1 (8) | PGMEA (1,000) | EL (1,000) | PGME (1,300) |
| Example 68 | Salt-1 (5.3) | Polymer 5 (80) | PAG-1 (8) | PGMEA (1,000) | EL (1,000) | PGME (1,300) |
| Example 69 | Salt-1 (5.4) | Polymer 6 (80) | PAG-1 (8) | PGMEA (1,000) | EL (1,000) | PGME (1,300) |
| Example 70 | Salt-1 (6.4) | Polymer 7 (80) | PAG-3 (10) | PGMEA (1,000) | EL (1,000) | PGME (1,300) |
| Example 71 | Salt-1 (5.1) | Polymer 8 (80) | PAG-1 (8) | PGMEA (1,000) | EL (1,000) | PGME (1,300) |
| Example 72 | Salt-1 (5.5) | Polymer 9 (80) | PAG-1 (8) | PGMEA (1,000) | EL (1,000) | PGME (1,300) |
| Example 73 | Salt-1 (6.8) | Polymer 10 (80) | PAG-3 (10) | PGMEA (1,000) | EL (1,000) | PGME (1,300) |
| Example 74 | Salt-1 (5.3) | Polymer 11 (80) | PAG-1 (8) | PGMEA (1,000) | EL (1,000) | PGME (1,300) |
| Example 75 | Salt-1 (5.3) | Polymer 12 (80) | PAG-1 (8) | PGMEA (1,000) | EL (1,000) | PGME (1,300) |
| Example 76 | Salt-3 (5.1) | Polymer 2 (80) | PAG-2 (8) | PGMEA (1,000) | EL (1,000) | PGME (1,300) |
| Example 77 | Salt-5 (5.4) | Polymer 3 (80) | PAG-2 (8) | PGMEA (1,000) | EL (1,000) | PGME (1,300) |
| Example 78 | Salt-8 (5.4) | Polymer 3 (80) | PAG-2 (8) | PGMEA (1,000) | EL (1,000) | PGME (1,300) |
| Example 79 | Salt-3 (5.1) | Polymer 2 (80) | PAG-2 (5) PAG-3 (5) | PGMEA (1,000) | EL (1,000) | PGME (1,300) |
| Example 80 | Salt-5 (5.4) | Polymer 3 (80) | PAG-2 (5) PAG-3 (5) | PGMEA (1,000) | EL (1,000) | PGME (1,300) |
| Example 81 | Salt-8 (5.4) | Polymer 3 (80) | PAG-2 (5) PAG-3 (5) | PGMEA (1,000) | EL (1,000) | PGME (1,300) |
| Example 82 | Salt-1 (5.1) | Polymer 8 (80) | PAG-2 (8) | PGMEA (1,000) | EL (1,000) | PGME (1,300) |
| Example 83 | Salt-1 (5.3) | Polymer 9 (80) | PAG-2 (8) | PGMEA (1,000) | EL (1,000) | PGME (1,300) |
| Example 84 | Salt-1 (5.2) | Polymer 8 (80) | PAG-4 (8) | PGMEA (1,000) | EL (1,000) | PGME (1,300) |
| Example 85 | Salt-1 (5.2) | Polymer 9 (80) | PAG-4 (8) | PGMEA (1,000) | EL (1,000) | PGME (1,300) |
| Example 86 | Salt-1 (3.5) | Polymer 16 (80) | PAG-1 (8) | PGMEA (1,000) | EL (1,000) | PGME (1,300) |
| Comparative Example 7 | Comparative Salt-3 (1.8) | Polymer 2 (80) | PAG-1 (8) | PGMEA (1,000) | EL (1,000) | PGME (1,300) |
| Comparative Example 8 | Comparative Salt-3 (1.9) | Polymer 3 (80) | PAG-1 (8) | PGMEA (1,000) | EL (1,000) | PGME (1,300) |
| Comparative Example 9 | Comparative Salt-4 (1.6) | Polymer 2 (80) | PAG-1 (8) | PGMEA (1,000) | EL (1,000) | PGME (1,300) |
| Comparative Example 10 | Comparative Salt-4 (1.6) | Polymer 3 (80) | PAG-1 (8) | PGMEA (1,000) | EL (1,000) | PGME (1,300) |

The resist compositions of the present invention shown in the Table 10 (Examples 49 to 86) contain a resin containing an acetal group and the salt represented by the general formula (1). The salt represented by the general formula (1) in these resist compositions, if the temperature of a later-described PEB is 90° C., functions as an acid diffusion control agent.

Electron Beam Lithography Evaluation (2)
(Examples 49 to 86, Comparative Examples 7 to 10)

The positive resist compositions prepared above (Examples 49 to 86, Comparative Examples 7 to 10) were spin-coated on a mask blank whose 152 mm square top surface is a chrome oxynitride film by using an ACT-M (Product from Tokyo Electron Limited) and pre-baked on a heated plate at 90° C. for 600 seconds to produce a resist film 90 nm thick. The film thickness of a resist film obtained was measured with an optical instrument nanospec (Product from Nanometrics Incorporated). The film thickness was measured at 81 in-plate positions of a blank substrate other than an outer edge portion within 10 mm from a blank outer circumference to calculate the average film thickness value and the ranges of the film thickness.

Moreover, the resist film was exposed with an electron beam exposure apparatus (Product from NuFlare Technology Inc.: EBM-5000plus, accelerating voltage; 50 keV), baked (PEB: post exposure bake) at 90° C. for 600 seconds, developed with 2.38% by mass of an aqueous solution of tetra methyl ammonium hydroxide to obtain a positive pattern. A resist pattern obtained was evaluated as follows.

A patterned mask blank produced was observed with top-down scanning electron microscope (SEM), the exposure does for resolving 400 nm 1:1 line and space (LS) by 1:1 was defined as an optimal exposure does ($\mu C/cm^2$), and the minimum dimension at the exposure does for resolving 400 nm 1:1 line and space (LS) by 1:1 was defined as limiting resolution and a 200 nm LS edge roughness (LER) was measured with SEM. It was visually determined whether the pattern shape is rectangular or not. To evaluate CDU (CD uniformity), the line width, subjected to the exposure does ($\mu C/cm^2$) for resolving a 400 nm 1:1 line and space by 1:1, was measured at 49 in-plate positions of a blank substrate other than an outer edge portion within 20 mm from a blank outer circumference to calculate 3σ value from a value obtained by deducting a measuring point from its average line width value. Each resist composition was evaluated and the results are shown in Table 11.

TABLE 11

| | Optimum exposure ($\mu C/cm^2$) | Limiting resolution (nm) | LER (nm) | CDU(3σ) (nm) | Pattern shape |
|---|---|---|---|---|---|
| Example 49 | 21 | 45 | 4.9 | 2.5 | Rectangular |
| Example 50 | 24 | 40 | 4.8 | 2.4 | Rectangular |
| Example 51 | 25 | 40 | 4.9 | 2.4 | Rectangular |
| Example 52 | 21 | 45 | 4.8 | 2.5 | Rectangular |
| Example 53 | 25 | 40 | 4.6 | 2.4 | Rectangular |
| Example 54 | 20 | 45 | 4.7 | 2.5 | Rectangular |
| Example 55 | 24 | 45 | 4.7 | 2.5 | Rectangular |
| Example 56 | 20 | 45 | 4.8 | 2.4 | Rectangular |
| Example 57 | 24 | 40 | 4.6 | 2.1 | Rectangular |
| Example 58 | 22 | 45 | 4.9 | 2.2 | Rectangular |
| Example 59 | 21 | 40 | 4.8 | 2.2 | Rectangular |
| Example 60 | 21 | 45 | 4.6 | 2.3 | Rectangular |
| Example 61 | 25 | 40 | 4.7 | 2.3 | Rectangular |
| Example 62 | 23 | 45 | 4.8 | 2.1 | Rectangular |
| Example 63 | 20 | 40 | 4.6 | 2.5 | Rectangular |
| Example 64 | 22 | 45 | 4.6 | 2.3 | Rectangular |
| Example 65 | 21 | 45 | 4.6 | 2.3 | Rectangular |
| Example 66 | 24 | 40 | 4.6 | 2.4 | Rectangular |
| Example 67 | 23 | 45 | 4.8 | 2.4 | Rectangular |
| Example 68 | 25 | 45 | 4.6 | 2.5 | Rectangular |
| Example 69 | 25 | 40 | 4.8 | 2.1 | Rectangular |
| Example 70 | 20 | 40 | 5.0 | 2.4 | Rectangular |
| Example 71 | 20 | 45 | 4.8 | 2.1 | Rectangular |
| Example 72 | 23 | 45 | 5.0 | 2.4 | Rectangular |
| Example 73 | 22 | 45 | 4.6 | 2.5 | Rectangular |
| Example 74 | 22 | 40 | 4.8 | 2.2 | Rectangular |
| Example 75 | 24 | 45 | 5.0 | 2.1 | Rectangular |
| Example 76 | 23 | 45 | 4.8 | 2.5 | Rectangular |
| Example 77 | 23 | 45 | 4.8 | 2.3 | Rectangular |
| Example 78 | 23 | 40 | 4.5 | 2.2 | Rectangular |
| Example 79 | 22 | 40 | 4.7 | 2.4 | Rectangular |
| Example 80 | 25 | 40 | 5.0 | 2.1 | Rectangular |
| Example 81 | 24 | 40 | 4.6 | 2.2 | Rectangular |
| Example 82 | 24 | 45 | 4.8 | 2.3 | Rectangular |
| Example 83 | 24 | 45 | 4.7 | 2.2 | Rectangular |
| Example 84 | 25 | 45 | 4.8 | 2.5 | Rectangular |
| Example 85 | 24 | 45 | 4.7 | 2.3 | Rectangular |
| Example 86 | 25 | 45 | 4.9 | 2.5 | Rectangular |
| Comparative Example 7 | 24 | 55 | 7.2 | 3.4 | Rectangular |
| Comparative Example 8 | 23 | 55 | 6.9 | 3.5 | Rectangular |
| Comparative Example 9 | 25 | 55 | 7.3 | 3.6 | Rectangular |
| Comparative Example 10 | 26 | 55 | 6.6 | 3.6 | Rectangular |

The results of the Table 11 will be described. The resist compositions containing the salt represented by the general formula (1) as an acid diffusion control agent (Examples 49 to 86) all showed favorable resolution and favorable pattern rectangular property, and LER was a favorable value. Meanwhile, resist compositions in Comparative Examples 7 to 10 by using benzoate or a salt having no fluorine atom at α position of a carboxyl group as an acid diffusion control agent showed unfavorable resolution, LER and CDU, compared to Examples. It is assumed that since the salt used in these Comparative Examples has a too large difference in pKa with benzenesulfonic acid generated from a photo acid generator, an ion exchange reaction cannot be caused, resulting in roughness deterioration.

As obviously described above, use of the resist composition of the present invention can provide an extremely high resolution, and enables a pattern with a low line edge roughness can be formed by exposure. The resist patterning process using the same is useful in manufacturing a semiconductor device, particularly in photo lithography for processing a photo mask blank.

It must be stated here that the present invention is not restricted to the embodiments shown by the above-mentioned embodiments. The above-mentioned embodiments are merely examples so that any embodiments composed of substantially the same technical concept as disclosed in the claims of the present invention and expressing a similar effect are included in the technical scope of the present invention.

What is claimed is:

1. A chemically-amplified positive resist composition for high energy beam exposure comprising: (A) a salt represented by the following general formula (1); and (B) a resin containing a repeating unit represented by the following general formula (U-1) that dissolves by acid action and increases solubility in an alkaline developer,

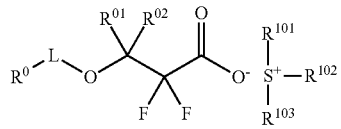
(1)

wherein R⁰ represents a hydrogen atom, or a linear monovalent hydrocarbon group having 1 to 20 carbon atoms or a branched or a cyclic monovalent hydrocarbon group having 3 to 20 carbon atoms with which a hetero atom may be substituted or in which a hetero atom may be included; each $R^{01}$ and $R^{02}$ independently represents a hydrogen atom, or a linear monovalent hydrocarbon group having 1 to 20 carbon atoms or a branched or a cyclic monovalent hydrocarbon group having 3 to 20 carbon atoms with which a hetero atom may be substituted or in which a hetero atom may be included, and $R^{01}$ and $R^{02}$ may mutually be bonded to form a cyclic structure together with a carbon atom bonded by the same and a carbon atom between the same, and at least one of $R^0$, $R^{01}$ and $R^{02}$ has a cyclic structure; each $R^{101}$, $R^{102}$ and $R^{103}$ independently represents a linear monovalent hydrocarbon group having 1 to 20 carbon atoms or a branched or a cyclic monovalent hydrocarbon group having 3 to 20 carbon atoms with which a hetero atom may be substituted or in which a hetero atom may be included, and two or more of $R^{101}$, $R^{102}$ and $R^{103}$ may mutually be bonded to form a cyclic structure together with a sulfur atom in the formula; and L represents a single bond, or any of an ester bond, a sulfonic acid ester bond, a carbonate bond, and a carbamate bond, each of which is formed together with an adjacent oxygen atom,

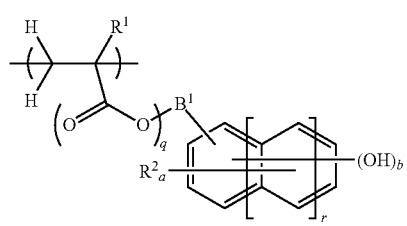
(U-1)

wherein "q" represents 0 or 1; "r" represents an integer of 0 to 2; $R^1$ represents any of a hydrogen atom, a fluorine atom, a methyl group, and a trifluoromethyl group; each $R^2$ independently represents a hydrogen atom or an alkyl group having 1 to 6 carbon atoms; $B^1$ represents a single bond, or an alkylene group having 1 to 10 carbon atoms that may contain an ether bond; "a" represents an integer satisfying a≤+2r−b; and "b" represents an integer of 1 to 3.

2. The resist composition according to claim 1, wherein the resin further contains a repeating unit represented by the following general formula (U-2),

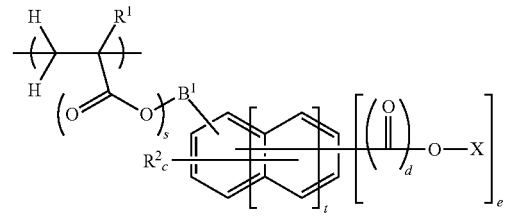
(U-2)

wherein "s" represents 0 or 1; "t" represents an integer of 0 to 2; $R^1$, $R^2$, and $B^1$ are the same as before; "c" represents an integer satisfying c≤+2t−e; "d" represents 0 or 1; "e" represents an integer of 1 to 3; and X represents an acid labile group if "e" represents 1 and a hydrogen atom or an acid labile group if "e" represents 2 or more, but at least one thereof represents an acid labile group.

3. The resist composition according to claim 1, wherein the resin further contains at least one of repeating units represented by the following general formulae (U-3) and (U-4),

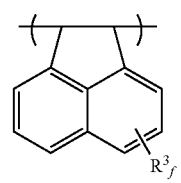
(U-3)

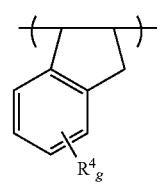
(U-4)

wherein "f" represents an integer of 0 to 6; each $R^3$ independently represents any of a hydrogen atom, an alkyl group or a primary or a secondary alkoxy group having 1 to 6 carbon atoms that may be halogen-substituted, and an alkylcarbonyloxy group having 1 to 7 carbon atoms that may be halogen-substituted; "g" represents an integer of 0 to 4; each $R^4$ independently represents any of a hydrogen atom, an alkyl or a primary or a secondary alkoxy group having 1 to 6 carbon atoms that may be halogen-substituted, and an alkylcarbonyloxy group having 1 to 7 carbon atoms that may be halogen-substituted.

4. The resist composition according to claim 2, wherein the resin further contains at least one of repeating units represented by the following general formulae (U-3) and (U-4),

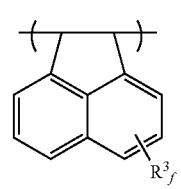
(U-3)

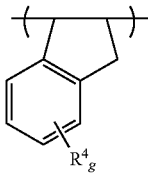

(U-4)

wherein "f" represents an integer of 0 to 6; each $R^3$ independently represents any of a hydrogen atom, an alkyl group or a primary or a secondary alkoxy group having 1 to 6 carbon atoms that may be halogen-substituted, and an alkylcarbonyloxy group having 1 to 7 carbon atoms that may be halogen-substituted; "g" represents an integer of 0 to 4; each $R^4$ independently represents any of a hydrogen atom, an alkyl or a primary or a secondary alkoxy group having 1 to 6 carbon atoms that may be halogen-substituted, and an alkylcarbonyloxy group having 1 to 7 carbon atoms that may be halogen-substituted.

5. The resist composition according to claim 1, wherein the resist composition further contains an acid generator that generates sulfonic acid by the high energy beam exposure.

6. The resist composition according to claim 2, wherein the resist composition further contains an acid generator that generates sulfonic acid by the high energy beam exposure.

7. The resist composition according to claim 3, wherein the resist composition further contains an acid generator that generates sulfonic acid by the high energy beam exposure.

8. The resist composition according to claim 4, wherein the resist composition further contains an acid generator that generates sulfonic acid by the high energy beam exposure.

9. The resist composition according to claim 1, wherein the resist composition further contains a basic compound.

10. The resist composition according to claim 2, wherein the resist composition further contains a basic compound.

11. The resist composition according to claim 3, wherein the resist composition further contains a basic compound.

12. The resist composition according to claim 4, wherein the resist composition further contains a basic compound.

13. The resist composition according to claim 5, wherein the resist composition further contains a basic compound.

14. The resist composition according to claim 6, wherein the resist composition further contains a basic compound.

15. The resist composition according to claim 7, wherein the resist composition further contains a basic compound.

16. The resist composition according to claim 8, wherein the resist composition further contains a basic compound.

17. A resist patterning process comprising steps of: applying the resist composition according to claim 1 on a substrate to be processed to obtain a resist film; pattern-exposing by a high energy beam; and developing by using an alkaline developer.

18. The resist patterning process according to claim 17, wherein an EUV or an electron beam is used as the high energy beam.

19. The resist patterning process according to claim 17, wherein a top surface of the substrate to be processed is composed of a material containing chrome.

20. The resist patterning process according to claim 17, wherein a photo mask blank is used as the substrate to be processed.

* * * * *